United States Patent [19]

Wacker et al.

[11] Patent Number: 5,264,431
[45] Date of Patent: Nov. 23, 1993

[54] POLYCYCLIC CONJUGATES

[75] Inventors: Oskar Wacker, Basle; Peter Traxler, Schönenbuch, both of Switzerland

[73] Assignee: Ciba-Geigy Corp., Ardsley, N.Y.

[21] Appl. No.: 973,133

[22] Filed: Nov. 6, 1992

[30] Foreign Application Priority Data

Nov. 7, 1991 [CH]  Switzerland ............... 3244/91
Sep. 9, 1992 [CH]  Switzerland ............... 2828/92

[51] Int. Cl.$^5$ .................. C07D 498/22; A61K 31/55
[52] U.S. Cl. ...................................... 514/211; 540/545
[58] Field of Search ..................... 540/545; 514/211

[56]  References Cited
U.S. PATENT DOCUMENTS

| | | |
|---|---|---|
| 4,256,735 | 3/1981 | Durette et al. ............ 424/177 |
| 4,315,913 | 2/1982 | Durette ..................... 424/88 |
| 5,093,330 | 3/1992 | Caravatti et al. ........... 514/211 |

FOREIGN PATENT DOCUMENTS

| | | |
|---|---|---|
| 0118364 | 9/1984 | European Pat. Off. . |
| 0296110 | 12/1988 | European Pat. Off. . |
| 0383919 | 8/1990 | European Pat. Off. . |
| 2655500 | 6/1977 | Fed. Rép. of Germany . |
| 9109034 | 6/1991 | PCT Int'l Appl. . |

OTHER PUBLICATIONS

Takahashi, et al. "Potent Selective Inhibition of 7-0--Methyl UCN-01 Against Protein Kinase C" The Journal of Pharmacology and Experimental Therapeutics, vol. 255, No. 3 pp. 1218-1221 (1990).

*Primary Examiner*—Mukund J. Shah
*Assistant Examiner*—Philip F. Datlow
*Attorney, Agent, or Firm*—Irving M. Fishman; Karen G. Kaiser; Barbara J. Ikeler

[57]  ABSTRACT

Staurosporin derivatives of the formula I are described,

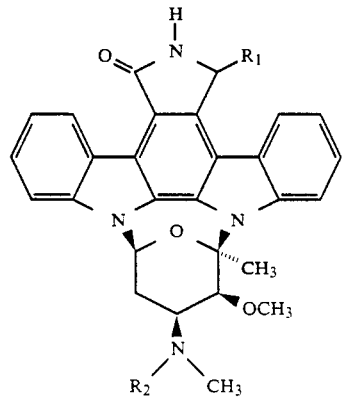

in which $R_1$ is hydrogen, hydroxyl, lower alkoxy or oxo and $R_2$ is a radical of the formula II

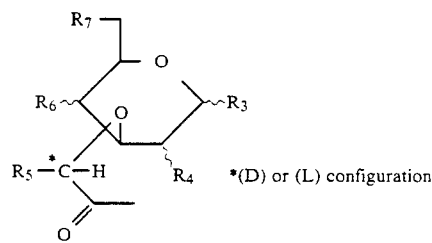

in which the configuration of the sugar moiety is derived from D-glucose, D-galactose or D-mannose, and $R_3$–$R_7$ are as defined below.

These compounds have a pronounced and selective inhibitory action on the enzyme proteinkinase C and have, inter alia, an antitumor action.

16 Claims, No Drawings

POLYCYCLIC CONJUGATES

The invention relates to staurosporin derivatives which are conjugated covalently with muramic acid derivatives, to processes for their preparation, to pharmaceuticals comprising these compounds, and to their use for the therapeutic treatment of warm-blooded species.

Staurosporin, as the substance on which the compounds according to the invention are based, was isolated as early as 1977 from cultures of *Streptomyces staurosporeus* AWAYA, TAKAHASHI and OMURA, sp. nov. AM 2282, cf. S. Omura et al., J. Antibiot. 30, 275-281 (1977), and tested for antimicrobial activity. In this context, it was also found that the compound is active against yeast-like microorganisms and fungi (MIC approximately 3-25 mcg/ml). Recently, extensive screening has shown, cf. T. Tamaoki et al., Biochem. and Biophys. Research Commun. 135 (No. 2), 397-402 (1986), that staurosporin has a powerful inhibitory action on proteinkinase C (from rat brain).

Proteinkinase C, which is dependent on phospholipids and calcium, can be found in several forms inside the cell and participates in a range of fundamental processes such as transmission of signals, proliferation and differentiation, as well as secretion of hormones and neurotransmitters. As is known, this enzyme is activated either via receptor-mediated hydrolysis of phospholipids of the cell membrane or by direct interaction with certain tumour-enhancing active ingredients. The sensitivity of the cell to the receptor-mediated signal transmission can be influenced substantially by altering the activity of proteinkinase C (as a signal transmitter). Compounds which are capable of influencing the activity of proteinkinase C can be used as antitumor, antiinflammatory, immunomodulating and antibacterial active ingredients and even be of interest as agents against artherosclerosis and diseases of the cardiovascular system and the central nervous system.

Even though staurosporin has a powerful inhibitory action on proteinkinase C (see above), it is also a powerful inhibitor of other proteinkinases and therefore does not have the selectivity which would be necessary for application in therapy.

It was the aim of the present invention to provide novel staurosporin derivatives which, even though selectively retaining the inhibitory activity of the staurosporin to proteinkinase C, are substantially less active with respect to other proteinkinases.

Surprisingly, it has now emerged that compounds which have a very potent inhibitory action on proteinkinase C but inhibit other proteinkinases only at a concentration which is higher by orders of magnitude, are obtained by covalent bonding of staurosporin derivatives to muramic acid derivatives.

In particular, the invention relates to staurosporin derivatives of the formula I

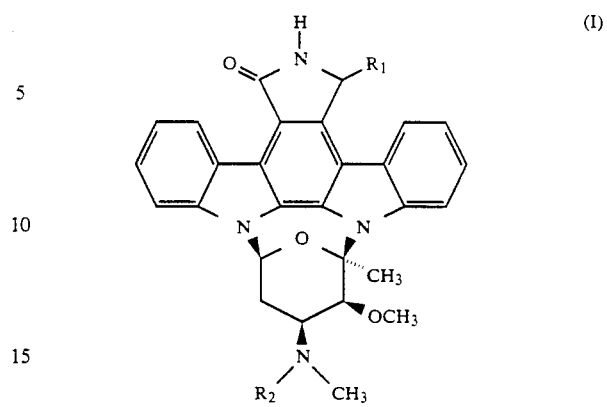

in which $R_1$ is hydrogen, hydroxyl, lower alkoxy or oxo and $R_2$ is a radical of the formula II

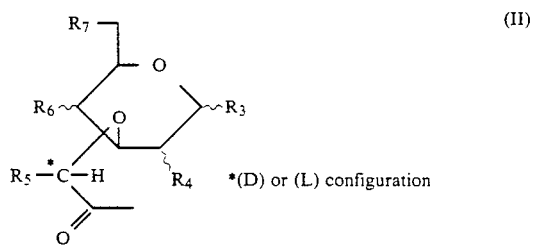

in which the configuration of the sugar moiety is derived from D-glucose, D-galactose or D-mannose, and $R_3$ is hydrogen, hydroxyl, lower alkanoyloxy, lower alkoxy, or benzyloxy, benzoyloxy or phenyloxy, each of which is unsubstituted or substituted in the phenyl moiety by halogen, hydroxyl, trifluoromethyl, lower alkyl or lower alkoxy, $R_4$ is hydroxyl, lower alkanoyloxy, benzoyloxy, benzyloxy, amino, lower alkylamino, di-lower alkylamino, lower alkoxycarbonylamino, $C_2$-$C_{20}$alkanoylamino, or benzoylamino, benzyloxycarbonylamino or phenyloxycarbonylamino, each of which is unsubstituted or substituted in the phenyl moiety by halogen, hydroxyl, trifluoromethyl, lower alkyl or lower alkoxy, $R_5$ is hydrogen or lower alkyl, $R_6$ is hydroxyl which is free or esterified with an aliphatic $C_2$-$C_{22}$ carboxylic acid, or is lower alkoxycarbonyloxy, lower alkylsulfonyloxy, amino which is free or acylated with an aliphatic $C_2$-$C_{22}$carboxylic acid, or is lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an aliphatic $C_2$-$C_{22}$carboxylic acid, or is lower alkoxycarbonyloxy, lower alkylsulfonyloxy, azido, amino which is free or acylated with an aliphatic $C_2$-$C_{22}$carboxylic acid, or is lower alkylamino, di-lower alkylamino, lower alkoxycarbonylamino, carbamoylamino, or is benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, to acid addition salts of these compounds with at least one salt-forming group, to processes for their preparation, to pharmaceuticals comprising these compounds, and to their use for the therapeutic treatment of warm-blooded animals.

The radicals terms hereinabove and hereinafter with the prefix "lower" contain up to and including 7, preferably up to and including 4, C atoms.

Lower alkoxy $R_1$ is preferably methoxy, ethoxy, propoxy or butoxy. From the sterical point of view, the radical $R_1$ can be in the $\alpha$- or $\beta$-position.

Radicals of the formula II in which the configuration of the sugar moiety is derived from D-glucose are preferred. These radicals are those of the formula III.

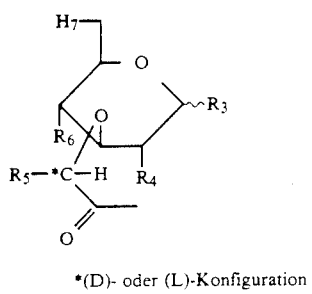

*(D)- oder (L)-Konfiguration

In the radicals of the formulae II and III, the configuration on the C-$R_5$ atom is, in the case of asymmetric substitution, i.e. when $R_5$ is other than hydrogen, L or preferably D, and the group $R_3$ is, in the event that $R_3$ is OH, in the $\alpha$- and $\beta$-position, and in the event that $R_3 \neq OH$, preferably in the $\alpha$-position.

The compounds of the formula I can also be regarded as derivatives of muramic acid, which has the formula IV.

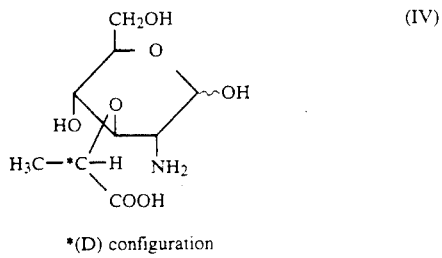

*(D) configuration

The corresponding acyl radical is termed "muramyl". (L)-muramic acid has the unnatural (L) configuration on the *C—CH$_3$. Demethylmuramic acid is a term for the compound of the formula IV in which the methyl group is replaced by hydrogen. Homomuramic acid is a term for the compound of the formula IV in which the methyl group is replaced by ethyl.

As can be seen, the compounds of the formula I are amides of muramic acid derivatives or of the diastereomers thereof.

Lower alkanoyloxy $R_3$ is preferably acetoxy or propionyloxy. Lower alkoxy $R_3$ is preferably methoxy or ethoxy.

Benzyloxy, benzoyloxy or phenyloxy $R_3$ is preferably unsubstituted. However, these radicals can also be substituent by one or more, but as a rule not more than three, identical or different phenyl substituents from those mentioned above.

Halogen as a phenyl substituent is preferably fluorine, chlorine or bromine, but additionally also iodine. Lower alkyl as substituent of a phenyl moiety is preferably methyl. Lower alkoxy as phenyl substituent is preferably methoxy.

Lower alkylamino $R_4$ is preferably methylamino or ethylamino. Di-lower alkylamino $R_4$ is preferably dimethylamino or diethylamino. Lower alkoxycarbonylamino $R_4$ is preferably tert-butyloxycarbonylamino. $C_2-C_{20}$alkanoylamino $R_4$ is preferably acetylamino or propionylamino. Benzoylamino, benzyloxycarbonylamino or phenyloxycarbonylamino $R_4$ is preferably unsubstituted. However, these radicals can also be substituted by one or more, but as a rule not more than three, identical or different phenyl substituents from those mentioned above. Phenylsulfonyloxy which is substituted by lower alkyl is preferably p-toluenesulfonyloxy.

Lower alkyl $R_5$ is preferably methyl, furthermore ethyl.

An aliphatic $C_2-C_{22}$carboxylic acid as esterification component of esterified hydroxyl or acylated amino $R_6$ or $R_7$ is, in particular, an unsubstituted aliphatic $C_2-C_{22}$carboxylic acid, in particular a $C_2-C_{22}$alkanoic acid or a $C_2-C_{22}$alkenoic acid, mainly an unbranched $C_2-C_{22}$alkanoic acid or an unbranched $C_2-C_{22}$alkenoic acid, preferably acetic acid or propionic acid, but additionally, in particular when the radical $R_7$ is concerned, also for example lauric acid, palmitic acid, stearic acid or oleic acid.

Lower alkoxycarbonyloxy $R_6$ or $R_7$ is, for example, tert-butyloxycarbonyloxy. Lower alkylsulfonyloxy $R_6$ or $R_7$ is preferably methylsulfonyloxy.

Benzoyloxy, benzyloxycarbonyloxy, benzoylamino, benzyloxycarbonylamino or phenylsulfonyloxy $R_6$ or $R_7$ or benzylamino $R_7$ is preferably unsubstituted. However, these radicals can also be substituted by one or more, but as a rule not more than three, identical or different phenyl substituents from those mentioned above.

The compounds of the formula I which have at least one basic group, for example a free amino group, as radical $R_4$ or $R_7$ can form acid addition salts, for example with inorganic acids such as hydrochloric acid, sulfuric acid or a phosphoric acid, or with suitable organic carboxylic or sulfonic acids, for example aliphatic mono- or dicarboxylic acids such as trifluoroacetic acid, acetic acid, propionic acid, glycol acid, succinic acid, maleic acid, fumaric acid, hydroxymaleic acid, malic acid, tartaric acid, citric acid, oxalic acid or amino acids such as arginine or lysine, aromatic carboxylic acids such as benzoic acid, 2-phenoxybenzoic acid, 2-acetoxybenzoic acid, salicylic acid, 4-aminosalicylic acid, araliphatic carboxylic acids such as mandelic acid or cinnamic acid, heteroaromatic carboxylic acids such as nicotinic acid or isonicotinic acid, aliphatic sulfonic acids such as methane-, ethane- or 2-hydroxyethanesulfonic acid, or aromatic sulfonic acids, for example benzene-, p-toluene- or naphthalene-2-sulfonic acid. If a plurality of basic groups is present, mono- or poly-acid addition salts can be formed.

For isolation or purification as well as in the case of the compounds which are further used as intermediates, salts which are not pharmaceutically acceptable can also be used. However, only the pharmaceutically utilisable, non-toxic salts are used for therapeutic use and are therefore preferred.

Due to the close relationship between the novel compounds in free form and in the form of salts thereof, including even those acid addition salts which can be used as intermediates, for example in the purification of the novel compounds or for their identification, the free compounds hereinabove and hereinafter are analogously understood as meaning the corresponding salts, if appropriate.

The compounds of the formula I have valuable pharmacological properties, for example they are selective inhibitors of the enzyme proteinkinase C. To determine the inhibitory action on proteinkinase C, proteinkinase C from pigs' brain is used which is purified following the procedure described by T. Uchida and C. R. Filburn in J. Biol. Chem. 259, 12311-4 (1984). The inhibitory action of the compounds of the formula I on proteinkinase C is determined by the methodology of D. Fabbro et al., Arch. Biochem. Biophys. 239, 102-111 (1985). In this test, the compounds of the formula I inhibit proteinkinase C already at a concentration $IC_{50}$ between approximately 0.001 and 0.05 μmol/liter. In contrast, the compounds of the formula I inhibit other enzymes, for example proteinkinase A, protein-phosphorylase-kinase and protein-tyrosin-kinase, only at a much higher concentration, for example a 100 times higher concentration. This demonstrates the selectivity of the compounds of the formula I.

As can already be expected on the basis of the abovementioned inhibitory action on proteinkinase C, the compounds of the formula I have antiproliferative properties which can be demonstrated directly in the following, different experiment: in this experiment, the inhibitory action of the compounds of the formula I on the growth of human T24 bladder carcinoma cells is determined. These cells are incubated in "Eagle's minimal essential medium" to which 5% (v/v) of foetal calf serum are added, in a humified incubator at 37° C. and 5 percent by volume of $CO_2$ in the air. The carcinoma cells (1000-1500) are transferred to 96-well microtitre plates and incubated overnight under the abovementioned conditions. Serial dilutions of the test substance are added on day 1. The plates are incubated for 5 days under the abovementioned conditions. During this period, the control cultures undergo at least 4 cell divisions. After the incubation, the cells are fixed using 3.3% (w/v) aqueous glutaraldehyde solution, washed with water and stained with 0.05% (weight/volume) aqueous Methylene Blue solution. After rinsing, the stain is eluted using 3% (w/v) aqueous hydrochloric acid. After this, the optical density (OD) per well, which is directly proportional to the number of cells, is measured at 665 nm using a photometer (Titertek multiskan). The $IC_{50}$ values are calculated with a computer system using the formula $$\frac{OD_{665} \text{ (test) minus } OD_{665} \text{ (beginning)}}{OD_{665} \text{ (control) minus } OD_{665} \text{ (beginning)}} \times 100$$

The $IC_{50}$ values are defined as the concentration of active ingredient at which the number of cells per well at the end of the incubation time is only 50% of the number of cells in the control cultures. For the compounds of the formula I, the $IC_{50}$ values which have been determined in this manner are between approximately 0.01 and 0.4 μmol/liter.

Due to the abovedescribed properties, the compounds of the formula I can be used, in particular, as antitumour active ingredients, for example for the therapy of tumours of the bladder. They are furthermore suitable for further applications mentioned above in the case of the proteinkinase C modulators, and they can be used, in particular, for the treatment of diseases which respond to proteinkinase C inhibition.

Preferred compounds of the formula I are those in which $R_3$ is hydroxyl, lower alkanoyloxy, lower alkoxy, or benzyloxy, benzoyloxy or phenyloxy, each of which is unsubstituted or substituted in the phenyl moiety by halogen, hydroxyl, trifluoromethyl, lower alkyl or lower alkoxy, and $R_4$ is amino, lower alkylamino, di-lower alkylamino, lower aloxycarbonylamino, $C_2$-$C_{20}$alkanoylamino, or benzoylamino, benzyloxycarbonylamino or phenyloxycarbonylamino, each of which is unsubstituted or substituted in the phenyl moiety by halogen, hydroxyl, trifluoromethyl, lower alkyl or lower alkoxy, and/or in which $R_6$ is hydroxyl which is free or esterified with an unsubstituted aliphatic $C_2$-$C_{22}$carboxylic acid, preferably an unbranched $C_2$-$C_{22}$alkanoic acid or an unbranched $C_2$-$C_{22}$alkenoic acid, or is lower alkoxycarbonyloxy, lower alkylsulfonyloxy, amino which is free or acylated with an unsubstituted aliphatic $C_2$-$C_{22}$carboxylic acid, preferably an unbranched $C_2$-$C_{22}$alkanoic acid or an unbranched $C_2$-$C_{22}$alkenoic acid, or is lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an unsubstituted aliphatic $C_2$-$C_{22}$carboxylic acid, preferably an unbranched $C_2$-$C_{22}$alkanoic acid or an unbranched $C_2$-$C_{22}$alkenoic acid, or is lower alkoxycarbonyloxy, lower alkylsulfonyloxy, azido, amino which is free or acylated with an unsubstituted aliphatic $C_2$-$C_{22}$carboxylic acid, preferably an unbranched $C_2$-$C_{22}$alkanoic acid or an unbranched $C_2$-$C_{22}$alkenoic acid, or is lower alkylamino, di-lower alkylamino, lower alkoxycarbonylamino, carbamoylamino, or benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, in particular the abovementioned compounds of the formula I in which $R_1$ is hydrogen, and acid addition salts of such compounds with at least one salt-forming group.

Particularly preferred compounds of the formula I are those in which $R_1$ is hydrogen and $R_2$ is a radical of the formula II in which $R_3$ is hydroxyl, benzyloxy which is preferably in the α-position, or lower alkoxy which is preferably in the α-position, $R_4$ is lower alkanoylamino, $R_5$ is lower alkyl or hydrogen, $R_6$ is hydroxyl and $R_7$ is hydroxyl, lower alkylsulfonyloxy, azido or amino, and acid addition salts of such compounds with at least one salt-forming group.

Particularly preferred compounds of the formula I are those in which the configuration of the sugar moiety is derived from D-glucose and/or have the (D) configuration on the C* atom, and acid addition salts of such compounds with at least one salt-forming group. Very preferred are the compounds of the formula I in which the configuration of the sugar moiety is derived from D-glucose, $R_1$ is hydrogen and $R_2$ is a radical of the formula II in which $R_3$ is hydrogen, hydroxyl, benzyloxy, lower alkoxy or lower alkanoyloxy, $R_4$ is lower alkanoylamino, preferably $C_1$-$C_4$alkanoylamino, $R_5$ is lower alkyl, preferably $C_1$-$C_4$alkyl, or hydrogen, $R_6$ is hydroxyl or lower alkanoyloxy and $R_7$ is hydroxyl, lower alkylsulfonyloxy, preferably methylsulfonyloxy, azido, amino or alkanoyloxy having up to 24 C atoms, and corresponding compounds in which $R_7$ is p-toluenesulfonyloxy, and acid addition salts of such compounds with at least one salt-forming group.

Very particularly preferred compounds of the formula I are those in which the configuration of the sugar moiety is derived from D-glucose, $R_1$ is hydrogen and $R_2$ is a radical of the formula II in which $R_3$ is hydroxyl, benzyloxy or lower alkoxy, $R_4$ is lower alkanoylamino, $R_5$ is lower alkyl or hydrogen, $R_6$ is hydroxyl and $R_7$ is hydroxyl, lower alkylsulfonyloxy, azido or amino, and acid addition salts of such compounds with at least one salt-forming group.

Most preferred compounds of the formula I are those described in the Examples and acid addition salts of such compounds with at least one salt-forming group.

The compounds of the formula I and the acid addition salts of such compounds with at least one salt forming group are prepared by processes known per se. The process according to the invention comprises acylating an amine of the formula V

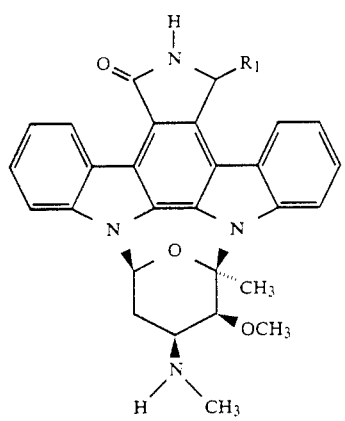

(V)

in which $R_1$ has the abovementioned meaning, with the proviso that, if required, a hydroxyl group represented by $R_1$ is protected by an easily detachable hydroxyl protective group, with a carboxylic acid of the formula VI (pyranose form)

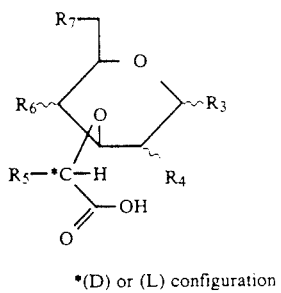

(VI)

*(D) or (L) configuration in which the substituents are as defined above, with the proviso that, if required, free functional groups which exist in a compound of the formula VI, with the exception of the carboxyl group participating in the reaction, are protected by easily detachable protective groups, or with a corresponding carboxylic acid in the furanose form, or with a reactive carboxylic acid derivative thereof, eliminating protective groups which do not exist in the desired end product of the formula I and, if desired, converting a resulting compound of the formula I with at least one salt-forming group into a different compound of the formula I or converting a resulting compound of the formula I into the acid addition salt thereof, or converting a resulting acid addition salt of a compound of the formula I into the free compound, and/or separating a resulting isomer mixture.

The procedure of the abovementioned process is illustrated hereinafter in greater detail:

A carboxylic acid in the furanose form which corresponds to the carboxylic acid of the formula VI is, for example, a compound of the formula VIII

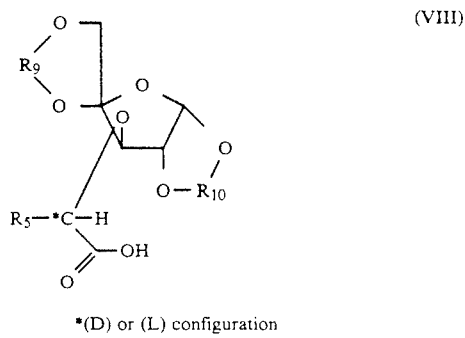

(VIII)

*(D) or (L) configuration in which $R_5$ is as defined above and $R_9$ and $R_{10}$ are in each case bivalent hydroxyl protective groups, or a compound of the formula IX

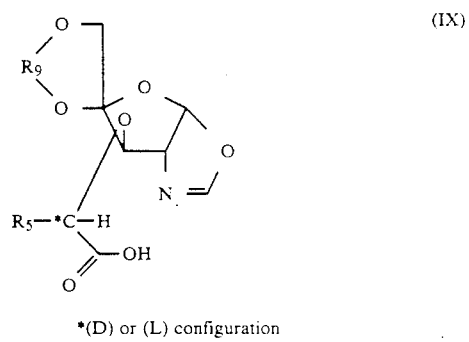

(IX)

*(D) or (L) configuration in which $R_5$ and $R_9$ are as defined above and $R_{11}$ is $C_1$-$C_{19}$alkyl or phenyl which is in each case unsubstituted or substituted in the phenyl moiety by halogen, protected hydroxyl, trifluoromethyl, lower alkyl or lower alkoxy. Suitable bivalent hydroxyl protective groups $R_9$ and $R_{10}$ are, for example, unsubstituted or substituted alkylidene or cycloalkylidene radicals, preferably unsubstituted or substituted lower alkylidene radicals, for example ethylidene, propylidene or, in particular, isopropylidene or benzylidene which can be substituted, for example, in the para-position of the phenyl moiety, or cycloalkylidene radicals, for example cyclopentylidene or cyclohexylidene.

GENERAL NOTES

The end substances of the formula I can contain substituents, for example $R_3$=benzyloxy, which can also be used as protective groups in starting substances for preparing other end substances of the formula I. This is why, within the scope of this text, only such as an easily detachable group is termed "protective group" which is not part of the specifically desired end substance of the formula I, unless specifically indicated otherwise in the context.

Functional groups in a compound of the formula VI which are best protected by easily detachable protective groups are mainly free amino groups, but also free hydroxyl groups.

Protective groups, their introduction and their detachment are described, for example, in "Protective Groups in Organic Chemistry", Plenum Press, London, N.Y. 1973, and in "Methoden der organischen Chemie", "[Methods in Organic Chemistry]", Houben-Weyl, 4th Edition, Vol. 15/1, Georg Thieme-Verlag, Stuttgart 1974, as well as in Theodora W. Greene, "Protective Groups in Organic Synthesis, John Wiley & Sons, New York 1981. It is characteristic of protective groups that they can be detached easily, i.e. without undesired secondary reactions taking place, for example by means of solvolysis, reduction, photolysis or else under physiological conditions.

Examples of hydroxyl protective groups are acyl radicals such as lower alkanoyl, unsubstituted or substituted, for example by halogen, such as 2,2-dichloroacetyl, or acyl radicals of carbonic acid monoesters, in particular tert-butyloxycarbonyl, unsubstituted or substituted benzyloxycarbonyl, for example 4-nitrobenzyloxycarbonyl, or diphenylmethoxycarbonyl, or 2-halo-lower alkoxycarbonyl such as 2,2,2-trichloroethoxycarbonyl, furthermore trityl or formyl, or organic silyl or stannyl radicals, furthermore easily detachable etherifying groups, such as tert-lower alkyl, for example tert-butyl, 2-oxa- or 2-thia-aliphatic or -cycloaliphatic hydrocarbon radicals, mainly 1-lower alkoxy-lower alkyl or 1-lower alkyl-thio-lower alkyl, for example methoxymethyl, 1-methoxyethyl, 1-ethoxyethyl, methylthiomethyl, 1-methylthioethyl or 1-ethylthioethyl, or 2-oxa- or 2-thia-cycloalkyl having 5–6 ring atoms, for example tetrahydrofuryl or 2-tetrahydropyranyl, or corresponding thia-analogues, as well as substituted or unsubstituted 1-phenyl-lower alkyl, such as unsubstituted or substituted benzyl or diphenylmethyl, examples of suitable substituents of the phenyl radicals being halogen, such as chlorine, lower alkoxy such as methoxy, and/or nitro.

A preferred protective group for the hydroxyl group $R_3$ ($R_3$=OH) in the 1-position of the sugar moiety of the compounds of the formula I is benzyl.

A protected amino group can be, for example, in the form of an easily cleavable acylamino, arylmethylamino, etherified mercaptoamino, 2-acyl-lower alk-1-enylamino, silylamino or stannylamino group, or as an azido group.

In a corresponding acylamino group, acyl is, for example, the acyl radical of an organic carboxylic acid having, for example, up to 18 carbon atoms, in particular of an alkanecarboxylic acid which is unsubstituted or substituted, for example by halogen or aryl, or a benzoic acid which is unsubstituted or substituted, for example by halogen, lower alkoxy or nitro, or of a carbonic acid monoester. Examples of such acyl groups are lower alkanoyl such as formyl, acetyl or propionyl, halo-lower alkanoyl, such as 2-haloacetyl, in particular 2-chloro-, 2-bromo-, 2-iodo-, 2,2,2-trifluoro- or 2,2,2-trichloroacetyl, or benzoyl which is unsubstituted or substituted, for example by halogen, lower alkoxy or nitro, for example benzoyl, 4-chlorobenzoyl, 4-methoxybenzoyl or 4-nitrobenzoyl, or lower alkoxycarbonyl which is branched in the 1-position of the lower alkyl radical or suitably substituted in the 1- or 2-position, in particular tert-lower alkoxycarbonyl, for example tert-butyloxycarbonyl, arylmethoxycarbonyl having one or two aryl radicals which are preferably phenyl which is unsubstituted or mono- or polysubstituted, for example by lower alkyl, in particular tert-lower alkyl, such as tert-butyl, lower alkoxy such as methoxy, hydroxyl, halogen, for example chlorine, and/or nitro, such as unsubstituted or substituted benzyloxycarbonyl, for example 4-nitrobenzyloxycarbonyl, or substituted diphenylmethoxycarbonyl, for example benzhydryloxycarbonyl or di-(4-methoxyphenyl)methoxycarbonyl, aroylmethoxycarbonyl, in which the aroyl group is preferably benzoyl which is unsubstituted or substituted, for example by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl in which the substituents independently of one another are in each case an aliphatic, araliphatic, cycloaliphatic or aromatic hydrocarbon radical having up to 15 C atoms, unsubstituted or substituted for example by lower alkyl, lower alkoxy, aryl, halogen or nitro, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethylsilyl)ethoxycarbonyl, or 2-triarylsilylethoxycarbonyl such as 2-triphenylsilylethoxycarbonyl.

Other acyl radicals which are suitable as amino protective groups are corresponding radicals of organic phosphoric acids, phosphonic acids or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, or di(phenyl-lower alkyl)phosphoryl which is unsubstituted or substituted, for example by nitro, for example dibenzylphosphoryl or di(4-nitrobenzyl)phosphoryl, or unsubstituted or substituted phenyloxyphenylphosphonyl, for example phenyloxyphenylphosphonyl, di-lower alkylphosphinyl, for example diethylphosphinyl, or unsubstituted or substituted diphenylphosphinyl, for example diphenylphosphinyl.

The aryl radicals in an arylmethylamino group which is a mono-, di- or, in particular, triarylmethylamino group, are, in particular, substituted or unsubstituted phenyl radicals.

Examples of such groups are benzyl-, diphenylmethyl- and, in particular, tritylamino.

An etherified mercapto group in an amino group which is protected with such a radical is mainly arylthio or aryl-lower alkylthio, in which aryl is, in particular, phenyl which is unsubstituted or substituted, for example by lower alkyl, such as methyl or tert-butyl, lower alkoxy, such as methoxy, halogen such as chlorine, and/or nitro. A corresponding amino protective group is, for example, 4-nitrophenylthio.

Acyl in a 2-acyl-lower alk-1-en-1-yl radical which can be used as an amino protective group is, for example, the corresponding radical of a lower alkanecarboxylic acid, of a benzoic acid which is unsubstituted or substituted, for example by lower alkyl such as methyl or tert-butyl, lower alkoxy such as methoxy, halogen such as chlorine, and/or nitro, or, in particular, of a carbonic acid monoester, such as a lower alkylmonoester of carbonic acid. Corresponding protective groups are mainly 1-lower alkanoylprop-1-en-2-yl, for example 1-acetylprop-1-en-2-yl, or 1-lower alkoxycarbonylprop-1-en-2-yl, for example 1-ethoxycarbonylprop-1-en-2-yl.

Preferred amino protective groups are acyl radicals of carbonic acid monoesters, in particular tert-butyloxycarbonyl, benzyloxycarbonyl which is unsubstituted or substituted, for example as indicated, for example 4-nitrobenzyloxycarbonyl, or diphenylmethoxycarbonyl, or 2-halo-lower alkoxycarbonyl, such as 2,2,2-trichloroethoxycarbonyl, furthermore trityl or formyl.

It is also possible to use protective groups which protect vicinal hydroxyl and/or amino groups together, it also being possible for such protective groups to be converted into desired substituents when the reaction has ended by the principle of latent functionality. For example, the hydroxyl group $R_3$ ($R_3$=OH) in the 1-position and the amino group $R_4$ in the 2-position of the sugar moiety can be protected together by a protective group of the formula

(VII)

in the form of a 2-oxazoline in which $R_8$ is lower alkyl or, preferably, phenyl. The 2-oxazoline is obtained by a series of processes known per se. For example, a compound of the formula VI having a protected carboxyl group in which $R_3$ is hydroxyl and $R_4$ is benzoylamino, can first be converted with HCl in acetyl chloride into the 1-chloride and the resulting compound can then be treated with a silver salt, for example AgNO$_3$, in collidine.

Alternatively, a compound of the formula VI having a protected carboxyl group in which $R_4$ is benzoylamino can be reacted in acetone with gaseous hydrogen chloride.

Cleavage of the resulting 2-oxazoline ring, which is particularly suitable for the preparation of n-benzoyl compounds of the formula I ($R_4$=benzoylamino), is effected using dilute acid, best at a pH of 2–4, for example 3, in the form of a one-pot reaction in a manner known per se, for example using an acetic ion exchanger, in particular an acetic ion exchanger having sulfonyl groups (such as Amberlite IR-120 (a styrene resin having strongly acidic sulfo groups) or Dowex 50 (polystyrenesulfonic acids) or a strong inorganic or organic acid such as hydrochloric acid, hydrobromic acid, sulfuric acid or a sulfonic acid, for example methanesulfonic acid, or a phenylsulfonic acid which is unsubstituted or substituted in the aromatic ring, such as p-toluenesulfonic acid, or trifluoroacetic acid. If the process is carried out in the presence of water, the result is a free hydroxyl group in the 1-position. If, in contrast, the process is carried out in the presence of alcohols, for example methanol, compounds in which $R_3$ is the radical of the alcohol in question are obtained.

The vicinal hydroxyl groups $R_6$ and $R_7$ are preferably protected by means of a joint alkylidene, preferably isopropylidene, or benzylidene group.

The protective groups which are not part of the desired end product of the formula I are detached in a manner known per se, for example by means of solvolysis, in particular hydrolysis, alcoholysis or acidolysis, or by means of reduction, in particular hydrogenolysis or chemical reduction, either stepwise or simultaneously.

A protected amino group is set free in a variety of ways, known per se and depending on the nature of the protective group, preferably by means of solvolysis or reduction. 2-Halo-lower alkoxycarbonylamino (if appropriate after having converted a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably salt-forming, reagent such as sodium thiophenolate, and 4-nitrobenzyloxycarbonylamino also by treatment with an alkali metal dithionite, for example sodium dithionite. Substituted or unsubstituted diphenylmethoxycarbonylamino, tert-lower alkoxycarbonylamino or 2-trisubstituted silylethoxycarbonylamino can be cleaved by treatment with a suitable acid, for example formic or trifluoroacetic acid, substituted or unsubstituted benzyloxycarbonylamino for example by means of hydrogenolysis, i.e. by treatment with hydrogen in the presence of a suitable hydrogenation catalyst, such as a palladium catalyst, substituted or unsubstituted triarylmethylamino or formylamino for example by treatment with an acid such as mineral acid, for example hydrochloric acid, or an organic acid, for example formic, acetic or trifluoroacetic acid, in the presence or absence of water, and an amino group which is protected by an organic silyl group can for example be set free by means of hydrolysis or alcoholysis. An amino group which is protected by 2-haloacetyl, for example 2-chloroacetyl, can be set free by treatment with thiourea in the presence of a base, or with a thiolate salt, such as an alkali metal thiolate, of the thiourea, followed by solvolysis, such as alcoholysis or hydrolysis, of the condensation product formed. An amino group which is protected by 2-substituted silylethoxycarbonyl can also be converted into the free amino group by treatment with a salt of hydrofluoric acid which provides fluoride anions.

A hydroxyl group which is protected by a suitable acyl group, an organic silyl group or by substituted or unsubstituted 1-phenyl-lower alkyl is set free analogously to an amino group which is protected correspondingly. Hydroxyl which is protected by substituted or unsubstituted 1-phenyl-lower alkyl, for example benzyl, is preferably set free by catalytic hydrogenation, for example in the presence of a palladium-on-charcoal catalyst. A hydroxyl group which is protected by 2,2-dichloroacetyl is set free for example by basic hydrolysis, a hydroxyl group which is etherified by tert-lower alkyl or by a 2-oxa- or 2-thia-aliphatic or -cycloaliphatic hydrocarbon radical by acidolysis, for example by treatment with a mineral acid or a strong carboxylic acid, for example trifluoroacetic acid. Hydroxyl which is etherified with an organic silyl radical, for example trimethylsilyl, can also be set free with a salt of hydrofluoric acid which provides fluoride anions, for example tetrabutylammonium fluoride.

If several protected functional groups are present, the protective groups are preferably selected in such a way that more than one group can be detached simultaneously, for example by means of acidolysis, such as by treatment with trifluoroacetic acid or formic acid, or by reduction, such as treatment with zinc and acetic acid, or with hydrogen and a hydrogenation catalyst, such as a palladium/charcoal catalyst. If the desired end substances contain protective groups, for example if $R_3$ is benzyloxy, those protective groups which are intended to be detached after the reaction has taken place are selected in such a way that they can be detached regioselectively, for example an amino group in the 2-position of the sugar moiety which is protected by benzyloxycarbonyl can be set free by mild catalytic hydrogenation, a benzyloxy group remaining as radical $R_3$ because its detachment requires more aggressive reaction conditions, for example a much longer reaction time.

A reactive acid derivative of a compound of the formula VI is, in particular, a reactive (activated) ester, a reactive anhydride or a reactive cyclic amide.

Reactive (activated) esters of an acid of the formula VI are, in particular, esters which are unsaturated on the linking carbon atom of the esterifying radical, for example esters of the vinyl ester type, such as the actual vinyl esters (which can be obtained, for example, by transesterification of a suitable ester with vinyl acetate; activated vinyl ester method), carbamoylvinyl esters (which can be obtained, for example, by treating the corresponding acid with an isoxazolium reagent; 1,2-oxazolium method or Woodward method), or 1-lower alkoxyvinyl esters (which can be obtained, for example, by treating the corresponding acid with a lower alkoxyacetylene; ethoxyacetylene method), or esters of the amidino type, such as N,N'-disubstituted amidino esters (which can be obtained, for example, by treatment of the corresponding acid with a suitable N,N'-disubstituted carbodiimide, for example N,N'-dicyclohexylcarbodiimide; carbodiimide method), or N,N-disubstituted amidino esters (which can be obtained, for example, by treatment of the corresponding acid with an N,N-disubstituted cyanamide; cyanamide method), suitable aryl esters, in particular phenyl esters which are suitably substituted by electron-attracting substituents (which can be obtained, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent such as N,N'-dicyclohexylcarbodiimide; activated aryl ester method), cyanomethyl esters (which can be obtained, for example, by treatment of the corresponding acid with chloroacetonitrile in the presence of a base; cyanomethyl ester method), thioesters, in particular unsubstituted or substituted phenylthioesters, for example phenolthioesters which are substituted by nitro (which can be obtained, for example, by treatment of the corresponding acid with unsubstituted or substituted thiophenols, for example nitro-substituted thiophenols, i.a. with the aid of the anhydride or carbodiimide method; activated thioester method), amino or amido esters (which can be obtained, for example, by treatment of the corresponding acid with an N-hydroxyamino or N-hydroxyamido, compound, for example N-hydroxysuccinimide, N-hydroxypiperidine, N-hydroxyphthalimide or 1-hydroxybenzotriazole, for example by the anhydride or carbodiimide method; activated N-hydroxy ester method) or silyl esters (which can be obtained, for example, by treatment of the corresponding acid with a silylating agent, for example hexamethyldisilazane, and which react easily with hydroxyl groups, but not with amino groups).

Anhydrides of an acid of the formula VI can be symmetric or, preferably, mixed anhydrides of this acid, for example anhydrides with inorganic acids, such as acid halides, in particular acid chlorides (which can be obtained, for example, by treatment of the corresponding acid with thionyl chloride, phosphorus pentachloride or oxalyl chloride; acid chloride method), azides (which can be obtained, for example, from a corresponding acid ester via the corresponding hydrazide and treatment of the latter with nitrous acid; azide method), anhydrides with carbonic acid monoderivatives, such as with suitable esters, for example lower alkyl monoesters of carbonic acid (which can be obtained, for example, by treatment of the corresponding acid with halo-lower alkyl esters, such as lower alkyl chloroformates, or with a 1-lower alkoxycarbonyl-2-lower alkoxy-1,2-dihydroquinoline, for example 1-lower alkoxycarbony-2-ethoxy-1,2-dihydroquinoline; method of the mixed O-alkyl carbonic acid anhydrides), or anhydrides with dihalogenated, in particular dichlorinated, phosphoric acid (which can be obtained, for example, by treatment of the corresponding acid with phosphorus oxychloride; phosphorus oxychloride method), or anhydrides with organic acids, such as mixed anhydrides with organic carboxylic acids (which can be obtained, for example, by treatment of the corresponding acid with a substituted or unsubstituted lower alkane- or phenylalkane carboxylic acid halide, for example phenylacetic acid chloride, pivalic acid chloride or trifluoroacetic acid chloride; mixed carboxylic anhydride method) or with organic sulfonic acids (which can be obtained, for example, by treatment of a salt, such as an alkali metal salt, of the corresponding acid, with a suitable organic sulfonyl halide, such as lower alkanesulfonyl chloride or arylsulfonyl chloride, for example methanesulfonyl chloride or p-toluenesulfonyl chloride; method of the mixed sulfonic anhydrides) as well as symmetric anhydrides (which can be obtained, for example, by condensation of the corresponding acid in the presence of a carbodiimide or of 1-diethylaminopropyne; symmetric anhydride method).

Suitable cyclic amides are, in particular, amides with five-membered diaza cycles of aromatic character, such as amides with imidazoles, for example imidazole (which can be obtained, for example, by treatment of the corresponding acid with N,N'-carbonyldiimidazole; imidazolide method), or pyrazoles, for example 3,5-dimethylpyrazole (which can be obtained, for example, via the acid hydrazide by treatment with acetylacetone; pyrazolide method).

Derivatives of acids of the formula VI which can be used as acylating agents can also be formed in situ. For example, N,N'-disubstituted amidino esters can be formed in situ by reacting the mixture of the starting material of the formula V and of the acid used as acylating agent in the presence of a suitable N,N'-disubstituted carbodiimide, for example N,N'-dicyclohexylcarbodiimide. Furthermore, amino esters or amido esters of the acids used as acylating agent can be formed in the presence of the starting material of the formula V to be acylated, by reacting the mixture of the corresponding acid starting materials and amino starting materials in the presence of an N,N'-disubstituted carbodiimide, for example N,N'-dicyclohexylcarbodiimide, and of an N-hydroxyamine or N-hydroxyamide, for example N-hydroxysuccinimide, in the presence or absence of a suitable base, for example 4-dimethylaminopyridine.

The reaction can be carried out in a manner known per se, the reaction conditions depending mainly on whether and how the carboxyl group of the acylating agent of the formula VI is activated, customarily in the presence of a suitable solvent or diluent or a mixture of these, and, if required, in the presence of a condensing agent which can also be an acid-binding agent, for example when the carboxyl group participating in the reaction is in the form of the anhydride, with cooling or heating, for example in a temperature range from approximately −30° C. to approximately +150° C., in particular from approximately 0° C. to +100° C., preferably from room temperature (approx. +20° C.) to +70° C., in an open or sealed reaction vessel and/or in the atmosphere of an inert gas, for example nitrogen. Customary condensing agents are, for example, carbodiimides, for example N,N'-diethyl-, N,N'-dipropyl-, N,N'-dicyclohexyl- or N-ethyl-N'-(3-dimethylaminopropyl)carbodiimide, suitable carbonyl compounds, for example carbonyldiimidazole, or 1,2-oxazolium compounds, for example 2-ethyl-5-phenyl-1,2-oxazolium 3'-sulfonate and 2-tertbutyl-5-methylisoxazolium perchlorate, or suitable acylamino compounds, for example 2-ethoxy-1-ethoxycarbonyl-1,2-dihydroquinoline. Customary acid-binding condensing agents are, for example, alkali metal carbonates or alkali metal hydrogen carbonates, for example sodium carbonate, sodium hydrogen carbonate, potassium carbonate or potassium hydrogen carbonate (customarily together with a sulfate), or organic bases such as, customarily, sterically hindered tri-lower alkylamines, for example N,N-diisopropyl-N-ethylamine.

A resulting compound of the formula I can be converted into a different compound of the formula I, for example by acylation of free hydroxyl $R_6$, $R_7$, $R_4$ or $R_3$ or free amino $R_4$, $R_6$ or $R_7$ or by detachment of a protective group, such as benzyl in the radical $R_3$ or a lower alkoxycarbonyl or benzyloxycarbonyl radical in the radical $R_4$, $R_6$ or $R_7$, or by converting azido $R_6$ or $R_7$ into amino.

The method of acylation of free hydroxyl $R_6$, $R_7$, $R_4$ or $R_3$ or free amino $R_4$, $R_6$ or $R_7$ is analogous to the above-described acylation of a compound of the formula V with a compound of the formula VI or a reactive acid derivative thereof. The method of detachment of the protective groups is also as described above.

The method of conversion of azido $R_6$ or $R_7$ into amino is by means of reduction. Suitable reducing agents are all those which can be used for converting an azide into an amine, and which does not attack normal, i.e. unactivated, ester or amide bonds under the reaction conditions. Particularly preferred is triphenylphosphine or hydrogen in the presence of a suitable catalyst, for example a palladium catalyst, Raney nickel catalyst or platinum catalyst. However, it is also possible to use reducing agents such as zinc in acetic acid, aluminum amalgam in a moist ether, titanium(III) chloride, tin(II) chloride/NaOH or complex boron or aluminum hydrides, for example sodium boranate, lithium alanate or sodium bis[2-methoxyethoxy]dihydridoaluminate.

If both $R_6$ and $R_7$ are azido, either both azido groups can be reduced or selectively only the azido group $R_7$ in the 6-position of the sugar moiety, for example using triphenylphosphine, depending on the reaction conditions. To reduce the 6-azido group with triphenylphosphine, stoichiometric amounts or a small excess, for example 25%, or phosphine are used, and the reaction is allowed to proceed, advantageously for approximately 1-30 hours, in an inert solvent, for example a cyclic ether, such as, in particular, absolute tetrahydrofuran, at approximately 20°-40° C. The 4- and 6-azido groups can successfully be reduced in absolute tetrahydrofuran or in a tetrahydrofuran.dimethylformamide mixture, with an excess, for example of 50 to 125%, of triphenylphosphine, over a period of 25-50 hours at 50°-70° C. To destroy the phosphinimine formed, concentrated ammonia solution is added after the reduction with triphenylphosphine, and the mixture is stirred for several hours, for example 7 to 50 hours, at room temperature.

The catalytic reduction is preferably carried out in alcohol/water mixtures, for example methanol/water mixtures, with an addition of a little acid, for example acetic acid or hydrochloric acid, at a temperature between approximately +5° C. and +70° C., and, if required, under pressure.

The reduction with the complex hydrides is preferably carried out at −30° C. to +20° C., for example 0° C., in an inert solvent, for example in a suitable ether.

The isolated pure yields obtained in the azide reduction are approximately 75 to 95% of theory. The azide reduction is carried out at temperatures between −30° C. and +70° C. in a suitable solvent and, if required, under pressure or under a protective gas, for example nitrogen or argon.

Acid addition salts of compounds of the formula I are obtained in the customary manner, for example by treatment with an acid or a suitable anion exchange reagent.

Acid addition salts can be converted into the free compounds in the customary manner, for example by treatment with a suitable basic agent.

Mixtures of isomers can be separated into the individual isomers in a manner known per se, for example, inter alia, by fractional crystallisation or chromatography.

The starting substances of the formulae V and VI are known or can be prepared by processes known per se. The starting substance of the formula V in which $R_1$ is hydrogen, i.e. staurosporin, is commercially available and can be prepared by fermentation using the strain Streptomyces staurosporeus. This strain was deposited at the Fermentation Research Institute, Japan, under the number FERM P-3725 in connection with the examined Japanese patent publication [kokoku] No. 57-53076, which was published on Nov. 11, 1982. Staurosporin derivatives of the formula V in which $R_1$ is other than hydrogen are described, for example, by I. Takahashi et al., J. Pharmacol. Exp. Ther. 255(3) (1990) 1218-1221. Muramic acid derivatives of the formula VI are described, for example, in British Patent 1 570 625, which is equivalent to French Patent 2 361 902, German Offenlegungsschrift 2 655 500 and the Japanese Patent Application having the Application Number 147903/76, and in German Patent 2 450 355 and in U.S. Pat. No. 4,256,735. Compounds of the formula VI in which $R_3$ is hydrogen are described, for example, in U.S. Pat. No. 4,315,913. The compounds of the formula VIII are described, for example, in the European Patent Application having the Application Number 84400413.5, which was published on Dec. 9, 1984 under the Publication Number 0 118 364. In general, the compounds of the formula VI are obtained by reacting the corresponding sugar derivative, 1-deoxy sugar derivative, 1-deoxyamino sugar derivative or amino sugar derivative having a free 3-hydroxyl group with a compound of the formula Hal—CH($R_5$)—COOH in which Hal is a leaving group, such as, in particular, suitable halogen, such as chlorine, in the presence of a strong base, such as sodium hydride, for example as described in the examples.

Unless stated otherwise, the above-described processes, including the processes for detaching protective groups and the additional measures related to the process, are carried out in a manner known per se, for example in the presence or absence of, preferably inert, solvents or diluents, if required in the presence of condensing agents or catalysts, at reduced or increased temperature, for example in a temperature range from approximately −20° C. to approximately 150° C., in particular from approximately 0° C. to approximately +70° C., preferably from approximately +10° C. to approximately +50° C., mainly at room temperature, in a suitable vessel and, if required, under an inert gas atmosphere, for example a nitrogen atmosphere.

Taking into account all substituents in the molecule, it may be required, for example in the presence of easily hydrolysable radicals, to use particularly mild reaction conditions, such as short reaction times, use of mild acidic or basic agents at a low concentration, stoichiometric ratios, selection of suitable catalysts, solvents, temperature conditions and/or pressure conditions.

The invention also relates to those embodiments of the process in which the starting material is a compound which can be obtained in any step of the process as an intermediate, and the missing process steps are carried out, or the process is terminated at any step, or a starting material is formed under the reaction conditions or used in the form of a reactive derivative or salt. It is preferred to use those starting materials which lead according to the invention to the compounds described above as being particularly valuable.

Novel starting materials and/or intermediates as well as processes for their preparation are also an object of the present invention. It is preferred to select starting materials and reaction conditions in such a way that the compounds mentioned in this application as being particularly preferred are obtained.

The invention also relates to the use of the compounds of the formula I and the pharmaceutically acceptable salts thereof, preferably in the form of pharmaceutical compositions, for the therapeutic treatment of the human or animal body, in particular in the case of the abovementioned diseases. The invention also relates to a method for inhibiting proteinkinase C in a warmblooded species requiring such a treatment, whereby an effective proteinkinase-C-inhibiting dose of a compound of the formula I or a pharmaceutically acceptable acid addition salt thereof is administered to this representative of a warm-blooded species. The dose of the active ingredient depends, inter alia, on the type of the disease, the nature and size of the species to be treated, the disposition of the organism with regard to immunity, and the way in which the active ingredient is administered. For example, a representative of a warmblooded species having a bodyweight of approximately 70 kg is administered a daily dose of 1 mg to 1500 mg, mainly 100 mg to 1000 mg, preferably 200 mg to 800 mg, for example 500 mg, of a compound of the formula I. This total daily dose is preferably split into 2-3 daily administrations. The dose in the case of oral administration is approximately two to three times higher than in the case of parenteral administration, i.e. rather in the upper range of the abovementioned doses.

The invention also relates to pharmaceutical compositions comprising an effective amount of the active ingredient, in particular an amount which is effective for the prophylaxis or therapy of one of the abovementioned diseases, together with pharmaceutically acceptable carriers which are suitable for topical, enteral, for example oral or rectal, or parenteral administration, and which can be inorganic or organic, solid or liquid. Compositions which are used for oral administration are, in particular, tablets or gelatine capsules which comprise the active ingredient together with diluents, for example lactose, dextrose, sucrose, mannitol, sorbitol, cellulose and/or glycerol, and/or lubricants, for example silica, talc, stearic acid or salts thereof, such as magnesium stearate or calcium stearate, and/or polyethylene glycol. Tablets can also comprise binders, for example magnesiumaluminium silicate, starches such as maize, wheat or rice starch, gelatine, methylcellulose, sodium carboxylmethylcellulose and/or polyvinylpyrrolidone and, if desired, disintegrants, for example starches, agar, algic acid or a salt thereof such as sodium alginate, and/or effervescent mixtures, or adsorbants, colorants, flavourings and sweeteners. The pharmacologically active compounds of the present invention can furthermore be used in the form of compositions which can be administered parenterally, or solutions for infusion. Such solutions are preferably isotonic aqueous solutions or suspensions, it being possible for those to be prepared prior to use, for example in the case of lyophilised compositions which comprise the pure active ingredient or the active ingredient together with a carrier, for example mannitol. The pharmaceutical compositions can be sterilised and/or comprise excipients, for example preservatives, stabilisers, wetting agents and/or emulsifiers, solubilisers, salts for regulating the osmotic pressure and/or buffers. The present pharmaceutical compositions which, if desired, can comprise further pharmacologically active substances such as antibiotics, are prepared in a manner known per se, for example by means of conventional mixing, granulating, sugar-coating, dissolving or lyophilisation processes and comprise from approximately 0.01% to 90%, in the case of lyophilisates up to 100%, in particular from approximately 0.1% to approximately 50%, mainly between 1% and 30%, of the active ingredient, or active ingredients, a concentration of active ingredient of below 1% being particularly suitable for compositions for topical administration.

The examples which follow illustrate the invention without any restriction whatsoever. The $R_f$ values are determined on silica gel thin-layer plates (Merck, Darmstadt, Germany). The ratio of the mobile phases to each other in the mobile phase mixtures used is indicated in parts by volume (v/v), and temperatures are indicated in degrees centigrade. The concentration c of the substance in the solvent (mixture) is indicated in percent (weight/volume) where the optical rotation is concerned.

Abbreviations: DCCI: dicyclohexylcarbodiimide; HOBT: 1-hydroxybenzotriazole.

EXAMPLE 1

3.74 g (3.99 mmol) of N-(1-α-O-benzyl-4,6-O-benzylidene-2-N-acetylmuramyl)-staurosporin, which has a remaining water content of 0.95 mol, are suspended in 100 ml of 80% acetic acid and the suspension is stirred for 4.5 hours at 60° C. The resulting yellow solution is then poured into 500 ml of ice-water, the colourless suspension is stirred for 1 hour at room temperature, and the crystals which have precipitated are filtered off with suction and washed with water. The resulting crude product is purified by colomn chromatography on 300 g of silica gel Si 60 (Merck 7734, 0.063-0.2 mm) in chloroform/ethanol (98:2; 15 ml fractions). The fractions 476-590 are combined and evaporated at 30° in a high vacuum. After recrystallisation of the residue from 200 ml of ethyl acetate, N-(1-α-O-benzyl-2-N-acetylmuramyl)staurosporin is obtained in the form of beige crystals of m.p. 224°–226° (sintering from 220°) whose residual water content is 0.82 mol; $[\alpha]_D^{20} = +188.1 \pm 2.1°$ (c=0.472; methanol), $R_f=0.12$ (chloroform:ethanol=95:5), $R_f=0.48$ (chloroform:methanol=9:1).

$C_{46}H_{49}O_{10}\cdot0.82\ H_2O$ (846.70); Calc. C 65.25 H 6.03 N 8.27 O 20.45 $H_2O$ 1.74. Found C 65.17 H 6.10 N 8.33 O 20.32 $H_2O$ 1.74.

The starting material is obtained as follows:

Step 1.1: 1.65 g (11 mmol) of 1-hydroxybenzotriazole and 2.27 g (11 mmol) of N,N'-dicyclohexylcarbodiimide are added at 0° to a solution of 4.71 g (10 mmol) of 1-α-O-benzyl-4,6-O-benzylidene-2-N-acetyl muramic acid in 200 ml of absolute N,N'-dimethylformamide, and the mixture is stirred for 3.5 hours at 0°.4.20 g (9 mmol) of staurosporin are subsequently added, and the resulting solution is stirred for 1.5 hours at 0° and for 21 hours at room temperature. To complete the reaction, a further addition of active ester solution of 1.57 g (3.3 mmol) of 1-α-O-benzyl-4,6-O-benzylidene-2-N-acetyl muramic acid, 0.55 g (3.7 mmol) of 1-hydroxybenzotriazole and 0.76 g (3.7 mmol) of N,N'-dicyclohexylcarbodiimide is made, and the mixture is stirred for a further 21 hours at room temperature. The resulting yellowish solution is treated with 300 ml of water and stirred for 1.5 hours at room temperature, and the crystals which have precipitated are filtered off with suction and washed with water. The aqueous phase is discarded. The filtered material is suspended in 100 ml of methylene chloride, the suspension is stirred for 1 hour at room temperature and filtered, the product is washed with methylene chloride, and the filtrate is evaporated to dryness in a high vacuum at 30°. The residue (yellow resin) is purified by column chromatography on 1 kg of silica gel (Merck 7754, 0.063–0.2 mm) in chloroform/ethanol (98:2; 25 ml fractions). The fractions 198–218 (of DC purity) and the fractions 181–187 and 219–235 (mixed fractions) are combined and evaporated to dryness in a high vacuum at 30°. The mixed fractions are purified again on 320 g of silica gel (Merck 7754, 0.063–0.2 mm) in chloroform/ethanol (98:2; 10 ml fractions). The fractions 88–123 are combined and also evaporated. After recrystallisation of the fractions, of DC purity, thus obtained from ethanol, N-(1-α-O-benzyl-4,6-O-benzylidene-2-N-acetylmuramyl) staurosporin is obtained in the form of beige crystals of m.p. 214°–216° (sintering from 210°) whose residual water content is 0.95 mol; $[\alpha]_D^{20} = +228.6° \pm 1.8°$ (c=0.560; methanol), $R_f=0.44$ (chloroform:ethanol=95:5), $R_f=0.85$ (chloroform:methanol=9:1).

$C_{53}H_{53}N_5O_{10}\cdot 0.95\ H_2O$ (937.15); Calc. C 67.93 H 5.90 N 7.47 O 18.69 $H_2O$ 1.83, Found C 67.71 H 6.02 N 7.49 O 18.79 $H_2O$ 1.83.

EXAMPLE 2

275 mg (0.32 mmol) of N-(1-α-O-benzyl-2-N-acetylmuramyl)staurosporin (see Example 1) having a residual water content of 0.82 mol are hydrogenated catalytically in 10 ml of absolute methanol with a total of 300 mg of 5% palladium/charcoal (Degussa E101N) for 69 hours under atmospheric pressure at room temperature. The catalyst is then removed by filtration and the filtrate is evaporated to dryness in a high vacuum at 30°. The residue (yellow foam) is dissolved in 3 ml of absolute methanol, and this solution is treated with 100 ml of ethyl acetate. After 100 ml of n-pentane have been added, the mixture is left to stand for 16 hours at room temperature. The crystals which have been precipitated are filtered off with suction and washed with n-pentane. Recyrstallisation from methanol/ethyl acetate (1:10) gives N-(2-N-acetylmuramyl)staurosporin (1-α,β-anomer mixture) in the form of colourless crystals of m.p. 257°–259° (sintering from 254°) having a residual water content of 1.5 mol; $[\alpha]_D^{20} = +195.5° \pm 2.0°$ (c=0.488; methanol), $R_f=0.44$ (chloroform:methanol=4:1), $R_f=0.77$ (chloroform:methanol:water=70:30:5).

$C_{39}H_{43}N_5O_{10}\cdot 1.50\ H_2O$ (768.82); Calc. C 60.93 H 6.03 N 9.11 O 23.93 $H_2O$ 3.51, Found C 61.13 H 6.13 N 8.94 O 23.81 $H_2O$ 3.52.

EXAMPLE 3

130 ml (5 mmol, theoretically) of a suspension of crude N-(4,6-O-isopropylidene-2-N-acetylmuramyl)-staurosporin (1-α,β-anomer mixture) in N,N'-dimethylformamide are treated with 260 ml of 60% acetic acid and stirred for 18 hours at room temperature. Solids are then filtered off with suction (N,N'-dicyclohexylurea), and the mother liquor is evaporated in a high vacuum at 40°. The residue is suspended in 100 ml of water, and the resulting suspension is stirred for 1.5 hours at room temperature. The crystals which have precipitated are filtered off with suction and washed with water. The filtrate is discarded. The crude product is purified by flash chromatography at 0.4 bar on 500 g of silica gel Si 60 (Merck 9385, 0.063–0.040 mm) in chloroform/methanol (9:1; 25 ml fractions). The fractions 60–120 are combined and evaporated to dryness in a high vacuum at 30°. The residue is dissolved in 30 ml of methanol, and the resulting solution is filtered through a millipore filter (Fluoropore, FGLP, 0.2 μm). The filtrate is evaporated to dryness in a high vacuum at 30°, the residue is taken up in 10 ml of hot methanol, and the resulting solution is treated with 200 ml of hot ethyl acetate. The suspension formed in this manner is cooled to room temperature with stirring, and stirring is continued for 1 hour at 0°. The crystals which have precipitated are filtered off with suction and washed with ethyl acetate. N-(2-N-Acetylmuramyl)staurosporin is obtained as a 1-α,β-anomer mixture in the form of beige crystals of m.p. 256°–258°, whose residual water content is 1.29 mol; $[\alpha]_D^{20} = +198.7° \pm 1.9°$ (c=0.536; methanol), $R_f=0.16$ (chloroform:methanol=9:1), $R_f=0.44$ (chloroform:methanol=4:1), $R_f=0.75$ (chloroform:methanol:water=70:30:5). $C_{39}H_{43}N_5O_{10}\cdot 1.29\ H_2O$ (765.04) Calc. C 61.23 H 6.01 N 9.15 O 23.61 $H_2O$ 3.04 Found C 61.20 H 5.94 N 9.37 O 23.43 $H_2O$ 3.03

The starting material is obtained as follows:

Step 3.1: 10 ml of 1N hydrochloric acid are added dropwise at 0° to a solution of 4.11 g (10 mmol; 2.43 mmol/g) of the sodium salt of 4,6-O-isopropylidene-2-N-acetylmuramic acid (1-α,β-anomer mixture) in 30 ml of water, this is then diluted with 50 ml of N,N'-dimethylformamide, and the mixture is evaporated to dryness in a high vacuum at 30°. The product is evaporated twice using in each case 50 ml of N,N'-dimethylformamide, giving 4,6-O-isopropylidene-2-N-acetylmuramic acid (1-α,β-anomer mixture), which is suspended in 200 ml of absolute N,N'-dimethylformamide without further purification. 1.80 g (12 mmol) of 1-hydroxybenzotriazole and 3.09 g (15 mmol) of N,N'-dicyclohexylcarbodiimide are added to this suspension at 0°, and this colourless suspension is stirred for 2 hours at 0°. 2.33 g (5 mmol) of staurosporin are then added, and stirring is continued for 1 hour at 0° and 20 hours at room temperature. To complete the reaction of the staurosporin, a further addition of an active ester solution of 2.11 g (5 mmol) of the sodium salt of 4,6-O-isopropylidene-2-N-acetylmuramic acid (preparation of the free acid as described), 0.9 g (6 mmol) of 1-hydroxybenzotriazole and 1.545 g (7.5 mmol) of N,N'-dicyclohexylcarbodiimide is subsequently made as described above (duration of the reaction 2 hours), and stirring is continued for 8 hours at room temperature until reaction of the staurosporin is complete. After a total reaction time of 30 hours, the resulting yellowish suspension is concentrated to 130 ml, and the crude 4,6-O-isopropylidene-2-N-acetylmuramyl staurosporin (1-$\alpha,\beta$-anomer mixture) contained in the product is used without further purification for the preparation of 2-N-acetylmuramyl staurosporin.

EXAMPLE 4

A solution of 0.339 g [2.95 mmol; 230 $\mu$l (d=1.474)] of methanesulfonyl chloride in 19 ml of absolute pyridine is added dropwise at $-15°$ in the course of 10 minutes to a solution of 1.97 g (2.33 mmol) of N-(1-$\alpha$-O-benzyl-2-N-acetylmuramyl)staurosporin compound having a residual water content of 0.82 mol in 19 ml of absolute pyridine. The resulting brown solution is stirred for 1 hour at $-15°$, for 2 hours at 0° and for 20 hours at room temperature. A further dropwise addition of a solution of 31 $\mu$l (0.4 mmol) of methanesulfonyl chloride in 3 ml of absolute pyridine is then made at $-15°$ in the course of 3 minutes, and the mixture is stirred for a further 10.5 hours at $-15°$ to room temperature. The solution is then poured into 300 ml of ice-water, the solvent is decanted off from the precipitated crude product, and the residue is stirred with 200 ml of diethyl ether. The resulting crystals are filtered off with suction and washed with diethyl ether. The crude product is purified by column chromatography on 200 g of silica gel Si 60 (Merck 7734; 0.063-0.2 mm) in chloroform/ethanol (98:2; 15 ml fractions). The fractions 185-340 are combined and evaporated to dryness in a high vacuum at 30°. After crystallisation from ethyl acetate/n-pentane (2:1; 150 ml in total), N-(6-O-mesyl-1-$\alpha$-O-benzyl-2-N-acetylmuramyl)staurosporin is obtained in the form of pale yellow crystals of m.p. 218°-219° (sintering from 215°) having a residual water content of 0.93 mol; $[\alpha]_D^{20}+184.1°\pm1.9°$ (c=0.527; methanol), $R_f=0.28$ (chloroform:ethanol=95:5), $R_f=0.88$ (chloroform:methanol=9:1).

$C_{47}H_{51}N_5O_{12}S \cdot 0.93$ $H_2O$ (926.77); Calc. C 60.91 H 5.75 N 7.56 O 22.32 S 3.46 $H_2O$ 1.81, Found C 61.00 H 5.91 N 7.53 O 22.10 S 3.44 $H_2O$ 1.81.

EXAMPLE 5

638 mg (9.8 mmol) of sodium azide (superpure) is added, at room temperature and with stirring, to a solution of 971 mg (1.05 mmol) of N-(6-O-mesyl-1-$\alpha$-O-benzyl-2-N-acetylmuramyl)staurosporin having a residual water content of 0.93 mol in 13 ml of absolute N,N'-dimethylformamide. The resulting yellowish suspension is stirred for 6 hours at 75°, then diluted with 250 ml of chloroform at room temperature and washed three times using 100 ml of water in each case. The chloroform phases are combined, dried over sodium sulfate and filtered, and the product is evaporated to dryness in a high vacuum at 30°. The residue (yellow resin) is dissolved in 50 ml of hot ethyl acetate and this solution is treated with 50 ml of hot n-pentane. The crystals which have precipitated after 16 hours at room temperature are filtered off with suction and washed with n-pentane. N-(6-Azido-1-$\alpha$-O-benzyl-2-N-acetyl-6-deoxymuramyl)staurosporin is obtained in the form of pale yellow crystals of m.p. 213°-216° (sintering from 202°), having a residual water content of 0.76 mol; $[\alpha]_D^{20}=+189.5°\pm2.1°$ (c=0.478; chloroform:methanol=1:1), $[\alpha]_D^{20}=+189.3°\pm2.0°$ (c=0.495; methanol), $R_f=0.17$ (chloroform:ethanol=95:5), $R_f=0.44$ (chloroform:methanol=9:1), $R_f=0.77$ (chloroform:methanol=4:1).

$C_{46}H_{48}N_8O_9 \cdot 0.76$ $H_2O$ (870.63); Calc. C 63.46 H 5.73 N 12.87 O 17.94 $H_2O$ 1.57, Found C 63.16 H 5.69 N 12.82 O 17.95 $H_2O$ 1.57.

EXAMPLE 6

354 mg (1.35 mmol) of triphenylphosphine (superpure) are added to a solution of 770 mg (0.88 mmol) of N-(6-azido-1-$\alpha$-O-benzyl-2-N-acetyl-6-deoxymuramyl)-staurosporin having a residual water content of 0.76 mol into 25 ml of absolute tetrahydrofuran (superpure), and the mixture is stirred for 12 hours at 45°. The resulting solution is then treated with 1.35 ml of 25% ammonia solution and stirring is continued for 21 hours at room temperature. The mixture is then diluted with 250 ml of chloroform and washed three times using 100 ml of water in each case. The chloroform phases are combined, dried over sodium sulfate and filtered, and the product is evaporated to dryness in a high vacuum at 30°. The residue (yellowish foam) is purified by flash chromatography at 0.3 bar on 250 g of silica gel Si 60 (Merck 9385; 0.063-0.040 mm) in chloroform/methanol (4:1; 15 ml fractions). The fractions 58-100 are combined and evaporated in a high vacuum at 30°. The residue is dissolved in 20 ml of methanol, this solution is treated with 630 $\mu$l of one-normal methanesulfonic acid in ethanol, and 100 ml of ethyl acetate are finally added. The resulting suspension is stirred for 0.5 hours at room temperature and for 1.5 hours at 0°, and the crystals which have precipitated are filtered off with suction and washed with ethyl acetate. After another recrystallisation from methanol/ethyl acetate (3:20), N-(6-amino-1-$\alpha$-O-benzyl-2-N-acetyl-6-deoxymuramyl)-staurosporin methanesulfonate is obtained in the form of pale yellow crystals of m.p. 239°-242° (decomp., sintering from 235°) having a residual water content of 2.86 mol; $[\alpha]_D^{20}=+172.1°\pm2.0°$ (c=0.488; methanol), $R_f=0.15$ (chloroform:methanol=4:1), $R_f=0.59$ (chloroform:methanol:water=70:30:5).

$C_{46}H_{50}N_6O_9 \cdot CH_3SO_3H \cdot 2.86$ $H_2O$ (978.57); Calc. C 57.69 H 6.15 N 8.59 O 24.30 S 3.28 $H_2O$ 5.27, Found C 57.84 H 5.86 N 8.67 O 24.19 S 3.13 $H_2O$ 5.27.

EXAMPLE 7

0.435 g (0.44 mmol) of N-(6-amino-1-$\alpha$-O-benzyl-6-deoxy-2-N-acetylmuramyl)staurosporin methanesulfonate having a residual water content of 2.86 mol are hydrogenated catalytically for 87 hours under atmospheric pressure at room temperature in 60 ml of absolute methanol with a total of 480 ml of 5% palladium charcoal (Degussa E101N). The catalyst is then filtered off, and the filtrate is evaporated to dryness in a high vacuum at 30°. The yellow crystalline residue is purified by column chromatography on 30 g of silica gel Si 60 (Merck; 0.063-0.200 mm) in chloroform/methanol/water (70:30:5; 5 ml fractions). The fractions 18-45 are combined and evaporated to dryness in a high vacuum at 30°. After recrystallisation of the residue from methanol/ethyl acetate (3:20), N-(6-amino-6-deoxy-2-N-acetylmuramyl)staurosporin (1-$\alpha,\beta$-anomer mixture) is obtained as a mixture with its methanesulfonate (contains 0.25 mol methanesulfonic acid) in the form of beige crystals which decompose above 225° and have a residual water content of 2.17 mol; $[\alpha]_D^{20} = +177.0° \pm 2.1°$ (c=0.469; methanol), $R_f=0.25$ (chloroform:methanol:water=70:30:5), $R_f=0.29$ (n-butanol:acetic acid:water=67:10:23), $R_f=0.53$ (ethyl acetate:n-butanol:pyridine:acetic acid:water=42:21:21:6:10).

EXAMPLE 8

355 mg (0.38 mmol) of N-(6-O-mesyl-1-α-O-benzyl-2-N-acetylmuramyl)staurosporin having a residual water content of 0.93 mol are hydrogenated catalytically for 117 hours under atmospheric pressure at room temperature in 30 ml of methanol/chloroform (28:2) with a total of 500 mg of 5% palladium/charcoal (Degussa E101N). The catalyst is then filtered off, and the filtrate is evaporated to dryness in a high vacuum at 30°. The residue is purified by column chromatography on 30 g of silica gel Si 60 (Merck 7734; 0.063–0.2 mm) in chloroform/ethanol (95:5; 10 ml fractions). The fractions 35–85 are combined and evaporated to dryness in a high vacuum at 30°. After recrystallisation of the residue from ethyl acetate, N-(6-O-mesyl-2-N-acetylmuramyl)staurosporin (1-α,β-anomer mixture) is obtained in the form of beige crystals which decompose above 170° and have a residual water content of 1.28 mol; $[\alpha]_D^{20} = +171.6° \pm 1.9°$ (c=0.514; methanol), $[\alpha]_D^{20} = +185.0° \pm 2.0°$ (c=0.50; dimethylformamide), $R_f=0.11$ (chloroform:ethanol=95:5), $R_f=0.41$ (chloroform:methanol=9:1), $R_f=0.81$ (chloroform:methanol=4:1).

$C_{40}H_{45}N_5O_{12}S \cdot 1.28\ H_2O$ (842.95); Calc. C 57.00 H 5.69 N 8.31 O 25.21 S 3.80 $H_2O$ 2.74, Found C 56.99 H 5.60 N 8.05 O* S 3.61 $H_2O$ 2.74 (*not determined).

EXAMPLE 9

40 ml of a suspension of crude N-(4,6-O-isopropylidene-2-N-acetyldemethylmuramyl)staurosporin (see Step 9.2; 1 mmol, theoretically) are treated with 80 ml of 60% acetic acid and the mixture is stirred for 23 hours at room temperature. After filtration of the resulting yellow suspension, the filtrate is evaporated in a high vacuum at 30° and the residue is stirred with 50 ml of water for 2 hours at room temperature. The crude product which has precipitated is filtered off with suction and purified by flash chromatography at 0.25 bar on 100 g of silica gel Si 60 (Merck 9385; 0.063–0.040 mm) in chloroform/methanol (9:1; 20 ml fractions). The fractions 40–65 are combined and evaporated to dryness in a high vacuum at 30°. The residue is dissolved in 30 ml of methanol, the resulting solution is treated with active carbon, the mixture is brought to the boil, and the suspension is filtered through a millipore filter (Fluoropore, FGLP, 0.2 μm) while still warm. The filtrate, which is almost colourless, is concentrated in vacuo at 30° to approx. 3 ml, treated with 10 ml of ethyl acetate and heated. After cooling, N-(2-N-acetyldemethylmuramyl)staurosporin (1-α,β-anomer mixture) is obtained in the form of beige crystals of m.p. 224°–226° (sintering from 208°) having a residual water content of 1.60 mol; $[\alpha]_D^{20} = +153.5° \pm 2.0°$ (c=0.495; dimethylformamide), $R_f=0.10$ (chloroform:methanol=9:1), $R_f=0.43$ (chloroform:methanol=4:1), $R_f=0.73$ (chloroform:methanol:water=70:30:5).

$C_{38}H_{41}N_5O_{10} \cdot 1.60\ H_2O$ (756.60): Calc. C 60.33 H 5.89 N 9.26 O 24.53 $H_2O$ 3.81. Found C 60.13 H 5.91 N 9.28 O 24.30 $H_2O$ 3.81.

The starting material is obtained as follows:

Step 9.1: 5.0 g (10.75 mmol) of the sodium salt of 1-α-O-benzyl-4,6-O-isopropylidene-2-N-acetyldemethylmuramic acid are hydrogenated catalytically in 50 ml of water at pH 7.0 with 1.0 g of 5% palladium/charcoal (Degussa E101N) for 20 hours under atmospheric pressure at room temperature. The catalyst is then filtered off, and the filtrate is evaporated to dryness in a high vacuum at 40°. The crude sodium salt of 4,6-O-isopropylidene-2-N-acetyldemethylmuramic acid (1-α,β-anomer mixture) is obtained as a colourless foam which is processed without further purification; $R_f=0.23$ (chloroform:methanol:water=70:30:5), $R_f=0.71$ (acetonitrile:water=3:1).

Step 9.2: A solution of 714 mg (approx. 2 mmol) of the crude sodium salt of 4,6-O-isopropylidene-2-N-acetyldemethylmuramic acid (1-α,β-anomer mixture) in 10 ml of water is treated at 0° with 2 ml of one-normal hydrochloric acid. The resulting solution is diluted with 40 ml of N,N'-dimethylformamide and evaporated to dryness in a high vacuum at 40°. The residue is resuspended twice in each case 40 ml of N,N'-dimethylformamide and reevaporated. The resulting crude 4,6-O-isopropylidene-2-N-acetyldemethylmuramic acid (1-α,β-anomer mixture) is suspended in 40 ml of absolute N,N'-dimethylformamide. To this suspension there are added at 0° 450 mg (3 mmol) of 1-hydroxybenzotriazole and 825 mg (4 mmol) of N,N'-dicyclohexylcarbodiimide, and the mixture is stirred for 2 hours at 0°. 446 mg (1 mmol) of staurosporine are then added, and the mixture is subsequently stirred for 1 hour at 0° and for 20 hours at room temperature. The resulting yellowish solution is then reacted directly to give N-(2-N-acetyldemethylmuramyl)staurosporin (detachment of the 4,6-O-isopropylidene group).

EXAMPLE 10

A suspension of 1.588 g (1.71 mmol) of N-(1-α-O-benzyl-4,6-O-benzylidene-2-N-acetyl-L-muramyl)staurosporin having a residual water content of 0.45 mol in 35 ml of methanol is refluxed with stirring for 1 hour after 0.23 g (0.908 mmol) of iodine (twice sublimated) has been added. The resulting orange suspension is evaporated to dryness in a high vacuum at 40° and the residue is taken up in 200 ml of chloroform. The chloroform solution is washed twice with in each case 50 ml of 0.1-normal sodium thiosulfate solution and once with 50 ml of water. The chloroform phases are combined, dried over sodium sulfate and filtered, and the filtrate is reevaporated. The residue (1.66 g) is purified by column chromatography on 250 g of silica gel Si 60 (Merck, 0.063–0.2 mm) in chloroform/ethanol (98:2; 15 ml fractions). The fractions 93–150 are combined and evaporated. After recrystallisation of the residue from ethyl acetate, N-(1-α-O-benzyl-2-N-acetyl-L-muramyl)staurosporin is obtained in the form of beige crystals of m.p. 230°–232° (sintering from 224°) having a residual water content of 1.13 mol; $[\alpha]_D^{20} = +117.4° \pm 2.1°$ (c=0.477; methanol), $R_f=0.28$ (chloroform:ethanol=95:5), $R_f=0.55$ (chloroform:methanol=9:1).

$C_{46}H_{49}N_5O_{10} \cdot 1.13\ H_2O$ (852.28); Calc. C 64.83 H 6.06 N 8.22 O 20.89 $H_2O$ 2.39, Found C 65.12 H 6.04 N 8.34 O 20.69 $H_2O$ 2.39.

EXAMPLE 11

The preparation of N-(2-N-acetyl-L-muramyl)staurosporin (1-α,β-anomer mixture) is carried out analogously to Example 2 by hydrogenation (23 hours at 46°

C.) of 200 mg of N-(1-α-O-benzyl-2-N-acetyl-L-muramyl)staurosporin (Pd/C 5%, Degussa E101N). The crude product is purified by silica gel chromatography. 55 mg are obtained in the form of an amorphous, colourless powder of m.p. 250°–255° decomp.; $R_f=0.17$ (ethyl acetate:methanol=9:1).

The starting material is obtained as follows:

Step 11.1: Analogously to Example 1, Step 1.1, 2.357 g (5 mmol) of 1-α-O-benzyl-4,6-O-benzylidene-2-N-acetyl-L-muramic acid, 0.826 g (5.5 mmol) of 1-hydroxybenzotriazole, 1.135 g (5.5 mmol) of N,N'-dicyclohexylcarbodiimide and 1.866 g (4 mmol) of staurosporin in 100 ml of N,N'-dimethylformamide give after a reaction time of a total of 22 hours (5 hours at 0°, 17 hours at room temperature), work-up by column chromatography [350 g of silica gel Si 60, Merck 7754, 0.063–0.2 mm, in chloroform/ethanol (98:2)] and crystallisation from ethyl acetate, N-(1-α-O-benzyl-4,6-O-benzylidene-2-N-acetyl-L-muramyl)staurosporin in the form of colourless crystals of m.p. 220°–222° (sintering from 216°) having a residual water content of 0.45 mol; $[α]_D^{20}= +103.7°±2.2°$ (c=0.463; methanol), $R_f=0.30$ (chloroform:ethanol=95:5), $R_f=0.65$ (chloroform:methanol=9:1).

$C_{53}H_{53}N_5O_{10}$. 0.45 $H_2O$ (928.14); Calc. C 68.59 H 5.85 N 7.55 O 18.01 $H_2O$ 0.87, Found C 68.90 H 5.92 N 7.67 O 17.75 $H_2O$ 0.88.

EXAMPLE 12

Analogously to Example 4, 1.145 g (1.34 mmol) of N-(1-α-O-benzyl-2-N-acetyl-L-muramyl)staurosporin having a residual water content of 1.13 mol, 0.198 g [1.72 mmol, 134.7 μl (d=1.454)] of methansulfonyl chloride (superpure) in 11.5 ml of absolute pyridine, give, after a reaction time of 19 hours without further addition of methanesulfonyl chloride and purification by column chromatography on 100 g of silica gel Si 60 (Merck 7734, 0.063–0.2 mm) in chloroform/ethanol (98:2; 10 ml fractions) after recrystallisation from ethyl acetate, N-(6-O-mesyl-1-α-O-benzyl-2-N-acetyl-L-muramyl)staurosporin in the form of yellowish crystals of m.p. 220°–221° (sintering from 215°) having a residual water content of 1.19 mol; $[α]_D^{20}+83.7°±2.0°$ (c=0.490; methanol/chloroform 1:1), $R_f=0.35$ (chloroform:ethanol=95:5), $R_f=0.75$ (chloroform:methanol=9:1).

$C_{47}H_{51}N_5O_{12}S$. 1.19 $H_2O$ (931.45); Calc. C 60.61 H 5.78 N 7.52 O 22.66 S 3.44 $H_2O$ 2.30, Found C 60.61 H 5.72 N 7.54 O 22.46 S 3.39 $H_2O$ 2.30.

EXAMPLE 13

Analogously to Example 5, 1.16 g (1.25 mmol) of N-(6-O-mesyl-1-α-O-benzyl-2-N-acetyl-L-muramyl)-staurosporin having a residual water content of 1.19 mol and 766 mg (11.78 mmol) of sodium azide (superpure) in 16 ml of absolute N,N'-dimethylformamide give, after a reaction time of 8 hours at 75° and recrystallisation from ethyl acetate/n-pentane (1:1), N-(6-azido-1-α-O-benzyl-2-N-acetyl-6-deoxy-L-muramyl)staurosporin in the form of beige crystals of m.p. 214°–216° (sintering from 208°) having a residual water content of 0.69 mol; $[α]_D^{20}= +76.6°±1.9°$ (c=0.522; chloroform/methanol 1:1), $R_f=0.41$ (chloroform:ethanol=95:5), $R_f=0.62$ (chloroform:methanol=9:1), $R_f=0.73$ (chloroform:methanol=4:1).

$C_{46}H_{48}N_9$. 0.69 $H_2O$ (869.37); Calc. C 63.55 H 5.73 N 12.89 O 17.83 $H_2O$ 1.43, Found C 63.42 H 5.75 N 12.86 O 18.03 $H_2O$ 1.43.

EXAMPLE 14

Analogously to Example 6, 841 mg (0.97 mmol) of N-(6-azido-1-α-O-benzyl-2-N-acetyl-6-deoxy-L-muramyl)staurosporin having a residual water content of 0.69 mol and 390 mg (1.48 mmol) of triphenylphosphine (superpure) in 28 ml of absolute tetrahydrofuran give, after a reaction time of 12 hours at 45°, treatment with 1.47 ml of 25% ammonia solution (6 hours, room temperature), flash chromatography at 0.3 bar on 250 g of silica gel Si 60 (Merck 9385, 0.63–0.04 mm) in chloroform/methanol (4:1; 25 ml fractions) followed by conversion of the free amine into the methanesulfonate and recrystallisation from methanol/ethyl acetate (3:20), N-(6-amino-1-α-O-benzyl-2-N-acetyl-6-deoxy-L-muramyl)staurosporin methanesulfonate as pale yellow crystals of m.p. 239°–241° (decomp., sintering from 237°) having a residual water content of 2.3 mol; $[α]_D^{20}=110.4°±2.2°$ (c=0.462; methanol), $R_f=0.19$ (chloroform:methanol=4:1), $R_f=0.70$ (chloroform:methanol:water=70:30:5).

EXAMPLE 15

Analogously to Example 7, 405 mg (0.42 mmol) of N-(6-amino-1-α-O-benzyl-2-N-acetyl-6-deoxy-L-muramyl)staurosporin methanesulfonate having a residual water content of 2.3 mol give, by means of catalytic hydrogenation with a total of 580 mg of 5% palladium/charcoal (Degussa E101N) after a hydrogenation time of 92 hours, purification by column chromatography [25 g of silica gel Si 60, Merck 7734, 0.063–0.2 mm, in chloroform/methanol/water (70:30:5)] and crystallisation from methanol/ethyl acetate (1:10) N-(6-amino-2-N-acetyl-6-deoxy-L-muramyl)staurosporin (1-α,β-anomer mixture) which is in the form of a mixture of free amine and methanesulfonate (contains 0.3 mol methanesulfonic acid), in the form of beige crystals which decompose above 218° and have a residual water content of 3.4 mol; $[α]_D^{20}= +75.7°±4.2°$ (c=0.235; methanol), $R_f=0.26$ (n-butanol:acetic acid:water=67:10:23), $R_f=0.48$ (ethyl acetate:n-butanol:pyridine:acetic acid:water=42:21:21:6:10).

EXAMPLE 16

Analogously to Example 8, 350 mg (0.376 mmol) of N-(6-O-mesyl-1-α-O-benzyl-2-N-acetyl-L-muramyl)-staurosporin having a residual water content of 1.19 mol give, by catalytic hydrogenation [450 mg of 5% palladium/charcoal (Degussa E101N)] in methanol (hydrogenation time 68 hours) and recrystallisation from methanol/chloroform (1:2), N-(6-O-mesyl-2-N-acetyl-L-muramyl)staurosporin as the α-anomer in the form of colourless crystals which decompose above 192° and have a residual water content of 1.3 mol; $[α]_D^{20}= +111.1°±2.1°$ (c=0,468; dimethylformamide), $R_f=0.37$ (chloroform:methanol=9:1), $R_f=0.60$ (chloroform:methanol=4:1), $R_f=0.88$ (chloroform:methanol:water=70:30:5).

$C_{40}H_{45}N_5O_{12}S$. 1.30 $H_2O$ (843.31); Calc. C 56.97 H 5.69 N 8.30 O 25.23 S 3.80 $H_2O$ 2.78, Found C 56.89 H 5.72 N 8.09 O 25.22 S 3.68 $H_2O$ 2.77.

EXAMPLE 17

80 mg of N-(1-α-O-methyl-4,6-O-benzylidene-2-N-acetyldemethylmuramyl)staurosporin in 2 ml of acetic acid and 1.2 ml of $H_2O$ are stirred for 2 hours at 55° to detach the benzylidene protective group. The reaction mixture is then poured into 50 ml of ethyl acetate/hexane (1:1), with stirring. The precipitate of crude N-(1-α-O-methyl-2-N-acetyldemethylmuramyl)staurosporin is filtered off, redissolved in ethyl acetate and reprecipitated using ethyl acetate/hexane (1:1). To remove benzaldehyde, the product is digested several times in diethyl ether. N-(1-α-O-Methyl-2-N-acetyldemethylmuramyl)staurosporin is obtained in the form of an amorphous, colourless powder of m.p. 247°. $R_f$=0.27 (ethyl acetate:methanol=9:1), $[α]_D^{20}$=+169.1°±2.1° (c=0.460; methanol).

The starting material is obtained as follows:

Step 17.1: A mixture of 729 mg (1.89 mmol) of 1-α-O-methyl-4,6-O-benzylidene-2-N-acetyldemethylmuramic acid, 20 ml of CHCl$_3$, 10 ml of isopropanol, 0.5 ml of H$_2$O, 506 mg (2.45 mmol) of DCCI and 376 mg (2.45 mmol) of HOBT is stirred for 1 hour at room temperature and subsequently treated with 1.05 g (2.26 mmol) of staurosporin. The reaction mixture is stirred for 20 hours at room temperature and then evaporated to dryness. The residue is dissolved in 200 ml of ethyl acetate, washed twice using saturated NaCl solution, dried and evaporated to dryness. Silica gel chromatography of the crude product gives the desired compound which still contains DCCI as impurity, and which is purified by repeated digesting in a small amount of cold CH$_2$Cl$_2$ and removal of the insoluble DCCI by filtration. Finally, the product is dissolved in a small amount of CH$_2$Cl$_2$ and precipitated using hexane. N-(1-α-O-methyl-4,6-O-benzylidene-2-N-acetyldemethylmuramyl)staurosporin is obtained as a colourless, amorphous powder of m.p. 235°; $R_f$=0.25 (ethyl acetate:methanol=9:1).

EXAMPLE 18

N-(1-α-O-benzyl-4,6-O-isopropylidene-2-N-acetyldemethylmuramyl)staurosporin is prepared analogously to Example 2, Step 2.1, from 300 mg (0.73 mmol) of 1-α-O-benzyl-4,6-O-isopropylidene-2-N-acetyldemethylmuramic acid and 409 mg (0.88 mmol) of staurosporin in the form of an amorphous, colourless powder; $R_f$=0.35 (ethyl acetate:methanol=98:2 and 0.27 (toluene:ethyl acetate=6:4). The intermediate obtained can be processed for example analogously to Example 9.

EXAMPLE 19

Analogously to Example 2, Step 2.1, 940 mg (2.22 mmol) of 1-α-O-benzyl-4,6-O-isopropylidene-2-N-acetyl-L-muramic acid, 460 mg (2.22 mmol) of DCCI, 333 mg (2.22 mmol) of HOBT and 940 mg (2.22 mmol) of staurosporin in 50 ml of DMF, give 420 mg of N-(1-α-O-benzyl-4,6-O-isopropylidene-2-N-acetyl-L-muramyl)staurosporin as an amorphous, colourless powder; $R_f$=0.53 (CH$_2$Cl$_2$:methanol=9:1), $R_f$=0.42 (ethyl acetate:methanol=95:5), $[α]_D^{20}$=+151.0±1.7 (c=0,6; methanol). The intermediate obtained can be processed, for example analogously to Example 9.

EXAMPLE 20

Analogously to Example 1, 327 mg (0.343 mmol) of N-(1-α-O-benzyl-4,6-O-benzylidene-2-N-acetyl-homomuramyl)staurosporin, having a residual water content of 0.99 mol in 10 ml of 80% acetic acid give, after 8 hours at 60° and purification of the crude product by column chromatography on 50 g of silica gel Si 60 (Merck 9385, 0.040-0.063 mm) in chloroform/ethanol (95:5, 15 ml fractions) and crystallisation of the fractions 35-65 from ethyl acetate, N-(1-α-O-benzyl-2-N-acetylhomomuramyl)staurosporin in the form of beige crystals of m.p. 217°-219° (sintering from 205°) having a residual water content of 1.22 mol; $[α]_D^{20}$=+182.2°±1.9° (c=0.540; chloroform:methanol=1:1).

The starting material is obtained as follows:

Step 20.1: Analogously to Example 1, Step 1.1, 486 mg (1.0 mmol) of 1-α-O-benzyl-4,6-O-benzylidene-2-N-acetylhomomuramic acid (described in Example 4 of German Offenlegungsschrift No. 2 655 500), 180 mg (1.2 mmol) of 1-hydroxybenzotriazole, 247 mg (1.2 mmol) of N,N'-dicyclohexylcarbodiimide and 373 mg (0.8 mmol) of staurosporin in 20 ml of N,N'-dimethylformamide give, after a reaction time of a total of 52 hours [9 hours at 0°, 43 hours at room temperature; after 5 hours at 0° and 24 hours at room temperature, a further 146 mg (0.3 mmol) of 1-α-O-benzyl-4,6-O-benzylidene-2-N-acetylhomomuramic acid, 54 mg (0.36 mmol) of 1-hydroxybenzotriazole and 75 mg (0.36 mmol) of N,N'-dicyclohexylcarbodiimide are added to achieve complete reaction of the staurosporin employed], purification by column chromatography (100 g of silica gel Si 60, Merck 9385, 0.040-0.063 mm) in chloroform (15 ml fractions) and crystallisation of the fractions 103-180 from ethyl acetate/n-pentane (1:2), N-(1-α-O-benzyl-4,6-O-benzylidene-2-N-acetylhomomuramyl)staurosporin in the form of beige crystals of m.p. 205°-207° (sintering from 203°), having a residual water content of 0.99 mol; $[α]_D^{20}$=+231.5°±1.9° (c=0.520; methanol).

EXAMPLE 21

Analogously to Example 20, 347 mg (0.37 mmol) of N-(1-α-O-benzyl-4,6-O-benzylidene-2-N-acetyl-L-homomuramyl)staurosporin having a residual water content of 0.73 mol in 10 ml of 80% acetic acid give, after 4 hours at 60°, purification of the crude product by column chromatography on 70 g of silica gel Si 60 (Merck 9385, 0.040-0.063 mm) in chloroform/methanol (99:1, 15 ml fractions) and crystallisation of the fractions 200-220 from ethyl acetate, N-(1-α-O-benzyl-2-N-acetyl-L-homomuramyl)staurosporin in the form of beige crystals of m.p. 229°-231° (sintering from 225°) having a residual water content of 1.15 mol; $[α]_D^{20}$=+64.0°±2.0° (c=0.50; chloroform:methanol=1:1).

The starting material is obtained as follows:

Step 21.1: Analogously to Example 20, Step 20.1, 486 mg (1.0 mmol) of 1-α-O-benzyl-4,6-O-benzylidene-2-N-acetyl-L-homomuramic acid, 180 mg (1.2 mmol) of 1-hydroxybenzotriazole, 247 mg (1.2 mmol) of N,N'-dicyclohexylcarbodiimide and 373 mg (0.8 mmol) of staurosporin in 20 ml of N,N'-dimethylformamide after a reaction time of a total of 53 hours (10 hours at 0°, 43 hours at room temperature; further addition of activated 1-α-O-benzyl-4,6-O-benzylidene-2-N-acetyl-L-homomuramic acid as described in Step 20.1), purification by column chromatography (120 g of silica gel Si 60, Merck 9385, 0.040-0.063 mm) in chloroform (15 ml fractions) and crystallisation of the fractions 320-500 from ethyl acetate/n-pentane (1:2), N-(1-α-O-benzyl-4,6-O-benzylidene-2-N-acetyl-L-homomuramyl)staurosporin in the form of beige crystals of m.p. 212°-214° (sintering from 208°) having a residual water content of 0.73 mol; $[α]_D^{20}$=+96.1°±1.8° (c=0.541; methanol).

EXAMPLE 22

Analogously to Example 2, 245 mg (0.28 mmol) of N-(1-α-O-benzyl-2-N-acetyl-L-homomuramyl)staurosporin having a residual water content of 1.15 mol, gives, by means of catalytic hydrogenation in 20 ml of methanol with a total of 400 mg of 5% palladium/charcoal (Degussa E101N) under atmospheric pressure at room temperature after a hydrogenation time of 93 hours and crystallisation of the crude product from methanol, N-(2-N-acetyl-L-homomuramyl)staurosporin (1-α-anomer) in the form of colourless crystals of m.p. 230°–232° (sintering from 224°) having a residual water content of 1.01 mol; $[\alpha]_D^{20} = +116.1° \pm 2.1°$ (c=0.472; N,N'-dimethylformamide).

EXAMPLE 23

77 mg (0.513 mmol) of 1-hydroxybenzotriazole and 106 mg (0.513 mmol) of N,N'-dicyclohexylcarbodiimide are added at 0° to a solution of 200 mg (0.428 mmol) of 1-α-O-benzyl-4,6-O-diacetyl-2-N-acetylmuramic acid in 10 ml of absolute N,N'-dimethylformamide, and the mixture is stirred for 3 hours at 0°. 179 mg (0.385 mmol) of staurosporin are subsequently added, and the resulting yellowish suspension is stirred for 1.5 hours at 0° and for 26 hours at room temperature. After this, a further addition of active ester solution of 40 mg (0.086 mol) of 1-α-O-benzyl-4,6-O-diacetyl-2-N-acetylmuramic acid, 17 mg (0.11 mmol) of 1-hydroxybenzotriazole and 22 mg (0.11 mmol) of N,N'-dicyclohexylcarbodiimide are then added to achieve complete reaction of the staurosporin employed, and stirring is continued for 18 hours at room temperature. The resulting yellowish suspension is treated with 30 ml of water, the mixture is stirred for one hour at room temperature, and the crystals which have precipitated are filtered off with suction and washed with water. The aqueous phase is discarded. The solid product is suspended in 10 ml of methylene chloride, the suspension is stirred for one hour at room temperature and filtered, the product is washed with methylene chloride, and the filtrate is evaporated to dryness in a high vacuum at 30°. The residue (yellow resin) is purified by column chromatography on 40 g of silica gel Si 60 (Merck 9385, 0.040–0.063 mm) in chloroform (10 ml fractions). The fractions 175–305 are combined and evaporated to dryness in a high vacuum at 30°. After recrystallisation of the residue (beige crystals) from ethyl acetate/cyclohexane (1:2), N-(1-α-O-benzyl-4,6-O-diacetyl-2-N-acetylmuramyl)staurosporin is obtained in the form of beige crystals of m.p. 189.2°–191.8° (sintering from 185°), having a residual water content of 0.48 mol; $[\alpha]_D^{20} = +175.7° \pm 1.9°$ (c=0.535; chloroform).

The starting material is obtained as follows:

Step 23.1: 2.645 g (25.91 mmol; 2.45 ml) of acetic anhydride (superpure, Fluka) is added to a solution of 4.09 g (8.64 mmol) of benzyl 1-α-O-benzyl-2-N-acetylmuramate in 90 ml of absolute pyridine and the mixture is stirred for 92 hours at room temperature. The resulting yellowish solution is concentrated in a high vacuum at 40° to approx. 20 ml and then treated with 100 ml of water. After the mixture has been stirred for 2 hours at room temperature, the crystals which have precipitated are filtered off with suction, washed with water and dried in a high vacuum at 50°. After recrystallisation from 200 ml of cyclohexane, benzyl 1-α-O-benzyl-4,6-O-diacetylmuramate is obtained in the form of colourless crystals of m.p. 102.2°–103.4° (sintering from 100°); $[\alpha]_D^{20} = +106.9° \pm 1.0°$ (c=1.024; chloroform).

Step 23.3: 900 mg (1.6 mmol) of benzyl 1-α-O-benzyl-4,6-O-diacetyl-2-N-acetylmuramate are hydrogenated catalytically for 40 minutes in 20 ml of absolute methanol with 200 mg of 10% palladium/charcoal under atmospheric pressure at room temperature. The catalyst is then filtered off, and the filtrate is evaporated to dryness in a high vacuum at 30°. After recrystallisation of the colourless, crystalline residue from 30 ml of cyclohexane/ethyl acetate (1:1), 1-α-O-benzyl-4,6-O-diacetyl-2-N-acetylmuramic acid is obtained the form of colourless crystals of m.p. 136.3°–137.2° (sintering from 132°); $[\alpha]_D^{20} = +122.5° \pm 1.9°$ (c=0.519; chloroform).

EXAMPLE 24

Analogously to Example 23, 692 mg (approx. 1.0 mmol) of crude 1-α-O-benzyl-4-O-acetyl-6-O-stearoyl-2-N-acetylmuramic acid, 195 mg (1.3 mmol) of 1-hydroxybenzotriazole, 268 mg (1.3 mmol) of N,N'-dicyclohexylcarbodiimide and 370 mg (0.8 mmol) of staurosporin in 20 ml of absolute N,N'-dimethylformamide give, after a reaction time of a total of 42 hours [4 hours at 0°, 38 hours at room temperature; after 2 hours at 0° and 20 hours at room temperature, a further 173 mg (0.25 mmol) of crude 1-α-O-benzyl-4-O-acetyl-6-O-stearoyl-2-N-acetylmuramic acid, 49 mg (0.325 mmol) of 1-hydroxybenzotriazole and 67 mg (0.325 mmol) of N,N'-dicyclohexylcarbodiimide are added to achieve complete reaction of the staurosporin employed], purification by column chromatography (140 g of silica gel Si 60, Merck 9385, 0.040–0.063 mm) in chloroform (15 ml fractions) and crystallisation of the fractions 140–240 from 16.5 ml of cyclohexane/ethyl acetate (15:1.5), N-(1-α-O-benzyl-4-O-acetyl-6-O-stearoyl-2-N-acetylmuramyl)staurosporin in the form of beige crystals of m.p. 131.4°–134.1° (sintering from 128°), having a residual water content of 0.45 mol; $[\alpha]_D^{20} = +152.5° \pm 2.0°$ (c=0.499; chloroform).

The starting material is obtained as follows:

Step 24.1: 4.529 g (14.95 mmol; 4.99 ml) of stearoyl chloride (pract., Fluka 90–95%) are added to a solution of 5.445 g (11.5 mmol) of benzyl 1-α-O-benzyl-2-N-acetyl-muramate in 110 ml of absolute pyridine, and the resulting solution is stirred for 24 hours at room temperature. The resulting brownish solution is concentrated in a high vacuum at 40° to approx. 20 ml, the brown suspension which is then obtained is treated with 100 ml of water and stirred for 2 hours at room temperature, and the aqueous phase is decanted off. The aqueous phase is discarded. The greasy residue is dissolved in 100 ml of chloroform, the solution is dried over sodium sulfate and filtered, and the product is evaporated to dryness in a high vacuum at 30°.

The crude product (beige resin) is purified by flash chromatography at 0.4 bar on 500 g of silica gel Si 60 (Merck 9385, 0.040–0.063 mm) in chloroform (20 ml fractions). The fractions 135–250 are combined and evaporated in a high vacuum at 30°. Benzyl 1-α-O-benzyl-6-O-stearoyl-2-N-acetylmuramate is obtained as a pale yellowish oil; $[\alpha]_D^{20} = +65.5° \pm 0.9°$ (c=1.077; chloroform).

Step 24.2: Analogously to Example 23, Step 23.1, 5.980 g (8.08 mmol) of benzyl 1-α-O-benzyl-6-O-stearoyl-2-N-acetylmuramate and 1.65 g (16.2 mmol; 1.53 ml) of acetic anhydride (superpure, Fluka) in 80 ml of absolute pyridine give, after a reaction time of 44 hours at room temperature and recrystallisation of the crude product from 50 ml of methanol, benzyl 1-α-O-benzyl-4-O-acetyl-6-O-stearoyl-2-N-acetylmuramate in the form of colourless crystals of m.p. 72.4°–73.2° (sintering from 70°); $[α]_D^{20} = +80.9° ±1.8°$ (c=0.544; chloroform).

Step 24.3: Analogously to Example 23, Step 23.2, 1.82 g (2.3 mmol) of benzyl 1-α-O-benzyl-4-O-acetyl-6-O-stearyl-2-N-acetylmuramate give, by means of catalytic hydrogenation under atmospheric pressure at room temperature in 40 ml of methanol with 0.4 of 10% palladium/charcoal (hydrogenation time 45 minutes) and purification of the crude product by column chromatography on 140 g of silica gel Si 60 (Merck 9385, 0.040–0.063 mm) in chloroform/methanol/water (70:30:5; 10 ml fractions) after combination of the fractions 21–36, 1-α-O-benzyl-4-O-acetyl-6-O-stearoyl-2-N-acetylmuramic acid as a yellowish foam, $R_f=0.50$ (chloroform:methanol = 7:3), which contains a residual small amount of a secondary product ($R_f$ value in the abovementioned solvent = 0.40) and which is processed without further purification.

EXAMPLE 25

A solution of 302 mg (0.35 mmol) of N-(1-deoxy-4,6-O-benzylidene-2-N-acetylmuramyl)staurosporin having a residual water content of 0.3 mol and a residual ethyl acetate content of 0.5 mol, in 12 ml of 80% acetic acid, is stirred for 7.5 hours at 60°. The mixture is then evaporated to dryness in a high vacuum at 40°, and the residue thus obtained (yellow crystals) is purified by column chromatography on 30 g of silica gel Si 60 (Merck 9385, 0.040–0.063 mm) in chloroform/ethanol (95:5; 10 ml fractions). The fractions 85–175 are combined and evaporated in a high vacuum at 30°. After recrystallisation of the residue from 30 ml of ethyl acetate, N-(1-desoxy-2-N-acetylmuramyl)staurosporin is obtained in the form of beige, slightly hygroscopic crystals of m.p. 241°–243° (sintering from 234°) having a residual water content of 1.24 mol; $[α]_D^{20} = +198.4° ±2.0°$ (c=0.489; methanol). The starting material is obtained as follows:

Step 25.1: 1.02 g (7.5 mmol) of zinc chloride (Merck, analytical grade) are added to a suspension of 1.026 g (5.00 mmol) of 1-deoxy-2-N-acetyl-D-glucosamine [A. Hasegawa et al., Agric. Biol. Chem. 1986, 50 (7), 1873] in 10 ml of benzaldehyde (superpure, Fluka) and the mixture is stirred for 52 hours at room temperature.

The resulting yellow solution is poured into a mixture of 50 ml of ice-water and 50 ml of toluene, and the resulting yellow suspension is stirred for 0.5 hours at room temperature. The crystals which have precipitated are filtered off and recrystallised from 30 ml of ethanol. 1-Deoxy-2-N-acetyl-4,6-O-benzylidene-D-glucosamine is obtained in the form of colourless, slightly hygroscopic crystals of m.p. 259°–261° (sintering from 254°) having a residual water content of 0.16 mol; $[α]_D^{20} = -53.4° ±1.0°$ (c=0.965; chloroform:methanol = 1:1).

Step 25.2: A suspension of 0.470 g (1.59 mmol) of 1-deoxy-2-N-acetyl-4,6-O-benzylidene-D-glucosamine having a residual water content of 0.16 mol, in 50 ml of absolute 1,4-dioxane (Merck, analytical grade), is treated, at 65°, with 0.256 g (6.40 mmol) of 60% sodium hydride in oil (pract. Fluka). The grey suspension is stirred for 2 hours under reflux and allowed to cool to 65°, and a solution of 0.138 ml (1.60 mmol) of S(−)-2-chloropropionic acid (superpure, Fluka) in 5 ml of absolute 1,4-dioxane is added dropwise in the course of 4 minutes. This mixture is stirred for 5 hours under reflux and for 17 hours at room temperature. 20 ml of water are then added dropwise, and the mixture is evaporated in a high vacuum at 30°. The residue is taken up in 100 ml of water, acidified with one-normal hydrochloric acid (pH1) and extracted twice using 150 ml of diethyl ether in each case. The organic phases are washed three times using 50 ml of water in each case, combined, dried over sodium sulfate and filtered, and the filtrate is evaporated in a high vacuum at 30°. The residue crystallises from 10 ml of ethyl acetate. 1-Deoxy-4,6-O-benzylidene-2-N-acetylmuramic acid is obtained in the form of colourless crystals of m.p. 255°–256° (sintering from 252°) having a residual water content of 0.04 mol; $[α]_D^{20} = -8.6° ±1.8°$ (c=0.544; methanol).

Step 25.3: A solution, kept at 0°, of 0.388 g (1.06 mmol) of 1-deoxy-4,6-O-benzylidene-2-N-acetylmuramic acid having a residual water content of 0.04 mol in 10 ml of N,N'-dimethylformamide is treated with 0.207 g (1.38 mmol) of 1-hydroxybenzotriazole and 0.285 g (1.38 mmol) of N,N'-dicylcohexylcarbodiimide, and the mixture is stirred for 3 hours at 0°. 0.495 g (1.06 mmol) of staurosporin are added to the resulting colourless suspension, and the mixture is stirred for 1 hour at 0° and for 15 hours at room temperature. 40 ml of water are then added and the mixture is stirred for a further 0.5 hours at room temperature. The crystals which have precipitated (N,N'-dicyclohexylurea) are filtered off with suction, washed with water, dried in vacuo and suspended in 20 ml of methylene chloride, and the suspension is stirred for 0.5 hours at room temperature. The crystals (N,N'-dicyclohexylurea) are subsequently refiltered, and the filtrate is evaporated to dryness in a high vacuum at 30°. The residue is purified by column chromatography on 100 g of silica gel Si 60 (Merck 9385, 0.040–0.063 mm) in chloroform/methanol (98:2). The pure fractions ($R_f=0.38$; chloroform/ethanol = 95:5) are combined and evaporated in vacuo at 40°. After recrystallisation of the residue from 5 ml of ethyl acetate, N-(1-deoxy-4,6-O-benzylidene-2-N-acetylmuramyl)staurosporin is obtained in the form of beige crystals of m.p. 246°–248° (sintering from 238°) having a residual ethyl acetate content of 0.5 mol and a residual water content of 0.3 mol; $[α]_D^{20} = +269.2° ±2.1°$ (c=0.483; chloroform).

EXAMPLE 26

Analogously to Example 23, 602 mg (1.0 mmol) of 4-O-acetyl-6-O-stearoyl-2-N-acetylmuramic acid (1-α-anomer) having a residual water content of 0.17 mol, 195 mg (1.3 mmol) of 1-hydroxybenzotriazole, 268 mg (1.3 mmol) of N,N'-dicyclohexylcarbodiimide and 373 mg (0.8 mmol) of staurosporin in 20 ml absolute N,N'-dimethylformamide give, after a reaction time of a total of 22 hours (4 hours at 0°, 18 hours at room temperature), purification by column chromatography (150 g of silica gel Si 60, Merck 9385, 0.040–0.063 mm) in chloroform/ethanol (95:5; 15 ml fractions) and further purification by column chromatography of the fractions 27–34 (100 g of silica gel Si 60, Merck 9385, 0.040–0.063 mm) in chloroform (from fraction 600, in chloroform/methanol [98:2], in each case 15 ml fractions), and recrystallisation of the fractions 624–639 from 5 ml of ethyl acetate, give N-(4-O-acetyl-6-O-stearoyl-2-N-acetylmuramyl)staurosporin (1-α-anomer) in the form of beige crystals of m.p. 152.2°–155.4° (sintering from 139°), having a residual water content of 0.45 mol; $[α]_D^{20} = +143.5° ±1.9°$ (c=0.528; methanol). The starting material is obtained as follows:

Step 26.1: 4.10 g (5.25 mmol) of benzyl 1-α-O-benzyl-4-O-acetyl-6-O-stearoyl-2-N-acetylmuramate are hydrogenated catalytically for 92 hours in 200 ml of absolute methanol with a total of 2.0 g of 5% palladium/charcoal (Degussa E101N) under atmospheric pressure at room temperature. The catalyst is then filtered off and the filtrate is evaporated to dryness in a high vacuum at 30°. The residue (colourless foam) is purified by column chromatography on 360 g of silica gel Si 60 (Merck 9385, 0.040–0.063 mm) in chloroform/methanol (4:1; 20 ml fractions). The fractions 120–390 are combined and evaporated in a high vacuum at 30°. The residue (colourless foam) is dissolved in 200 ml of chloroform, and the solution is treated with 50 ml of 0.1-normal hydrochloric acid and stirred for 5 minutes at room temperature. The chloroform phase is separated off and then washed with 100 ml of water, dried over sodium sulfate and filtered, and the filtrate is reevaporated. After recrystallisation of the residue from 15 ml of ethanol, 4-O-acetyl-6-O-stearoyl-2-N-acetylmuramic acid (1-α-anomer) is obtained in the form of colourless crystals of m.p. 148.2°–152.1° (sintering from 122°) having a residual water content of 0.17 mol and a sulfated ash content of 4.4% (from column chromatography); $[\alpha]_D^{20} = +43.1° \pm 1.7°$ (c=0.591; chloroform:methanol=1:1). The substance is processed without further purification.

EXAMPLE 27

Analogously to Example 23, 377 mg (0.97 mmol) of 4,6-O-diacetyl-2-N-acetylmuramic acid (1-α-anomer) having a residual water content of 0.55 mol, 195 mg (1.3 mmol) of 1-hydroxybenzotriazole, 268 mg (1.3 mmol) of N,N'-dicyclohexylcarbodiimide and 373 mg (0.8 mmol) of staurosporin in 20 ml of absolute N,N'-dimethylformamide give, after a reaction time of a total of 46 hours (4 hours at 0°, 42 hours at room temperature), purification by column chromatography (100 g of silica gel Si 60, Merck 9385, 0.040–0.063 mm) in chloroform (15 ml fractions; from fraction 200, in chloroform/methanol [98:2]) and recrystallisation of the fractions 285–350 from 10 ml of ethyl acetate, N-(4,6-O-diacetyl-2-N-acetylmuramyl)staurosporin (1-α-anomer) in the form of beige crystals of m.p. 215°–217° (sintering from 212°) having a residual water content of 1.61 mol; $[\alpha]_D^{20} = +177.6° \pm 2.2°$ (c=0.447; methanol). The starting material is obtained as follows:

Step 27.1: Analogously to Example 26, Step 26.1, 3.70 g (6.63 mmol) of benzyl 1-α-O-benzyl-4,6-O-diacetyl-2-N-acetylmuramate give by means of catalytic hydrogenation under atmospheric pressure at room temperature in 200 ml of methanol with a total of 1.5 g of 5% palladium/charcoal (Degussa E 101N; hydrogenation time 70 hours) and purification by column chromatography on 320 g of silica gel Si 60 (Merck 9385, 0.040–0.063 mm) in methylene chloride/methanol/water (70:30:5; 15 ml fractions) after combining and evaporating the fractions 78–150 the crude 4,6-O-diacetyl-2-N-acetylmuramic acid in the form of colourless crystals. These are dissolved in 60 ml of water, and the solution is brought to pH1 using 15 ml one-normal hydrochloric acid. The aqueous solution is then saturated with sodium chloride and extracted twice using 150 ml of ethyl acetate in each case. The organic phases are combined, dried over sodium sulfate and reevaporated. After crystallisation of the residue from 35 ml of ethyl acetate/n-pentane (1:6), 4,6-O-diacetyl-2-N-acetylmuramic acid (1-α-anomer) is obtained in the form of colourless, hydroscopic crystals of m.p. 85.8°–90.8° (sintering from 78°) having a residual water content of 0.55 mol; $[\alpha]_D^{20} = +57.5° \pm 2.2°$ (c=0.449; methanol).

EXAMPLE 28

Analogously to Example 23, 317 mg (0.48 mmol) of 1-α,4-O-diacetyl-6-O-stearoyl-2-N-acetylmuramic acid having a residual water content of 0.78 mol, 98 mg (0.65 mmol) of 1-hydroxybenzotriazole, 134 mg (0.65 mmol) of N,N'-dicyclohexylcarbodiimide and 233 mg (0.5 mmol) of staurosporin in 10 ml of absolute N,N'-dimethylformamide give, after a reaction time of a total of 46 hours (4 hours at 0°, 42 hours at room temperature), purification by column chromatography (50 g of silica gel Si 60, Merck 9385, 0.040–0.063 mm) in methylene chloride/methanol (99:1; 10 ml fractions) and crystallisation of the fractions 46–70 from 10 ml of ethanol/water (1:4), N-(1-α,4-O-diacetyl-6-O-stearoyl-2-N-acetylmuramyl)staurosporin in the form of beige crystals of m.p. 146.4°–148.2° (sintering from 142°) having a residual water content of 0.44 mol; $[\alpha]_D^{20} = +136.7° \pm 1.7°$ (c=0.580; methanol). The starting material is obtained as follows:

Step 28.1: 204 mg (2.0 mmol; 0.189 ml) of acetic anhydride are added to a solution of 782 mg (1.29 mmol) of 4-O-acetyl-6-O-stearoyl-2-N-acetylmuramic acid (1-α-anomer) having a residual water content of 0.17 mol, in 20 ml of absolute pyridine, and the mixture is stirred for 44 hours at room temperature. The resulting yellow solution is evaporated to dryness in a high vacuum at 30°. The residue (beige foam) is purified by column chromatography on 100 g of silica gel Si 60 (Merck 9385, 0.040–0.063 mm) in chloroform/methanol (7:3; 15 ml fractions). The fractions 19–26 are combined and reevaporated. The residue is dissolved in 50 ml of water, the resulting solution is acidified using one-normal hydrochloric acid (pH1) and extracted twice using 100 ml of ethyl acetate in each case. The organic phases are combined, dried over sodium sulfate and evaporated in vacuo. The residue (colourless foam) crystallises from 21 ml of diethyl ether/petroleum ether (1:20). 1-α,4-O-Diacetyl-6-O-stearoyl-2-N-acetylmuramic acid is obtained in the form of colourless crystals of m.p. 105.3°–107.5° which have a residual water content of 0.78 mol and contain a small amount of petroleum ether; $[\alpha]_D^{20} = +63.9° \pm 1.9°$ (c=0.532; methanol).

EXAMPLE 29

Analogously to Example 23, 235 mg (0.56 mmol) of 1-α,4,6-O-triacetyl-2-N-acetylmuramic acid having a residual water content of 0.14 mol, 109 mg (0.73 mmol) of 1-hydroxybenzotriazole, 150 mg (0.73 mmol) of N,N'-dicyclohexylcarbodiimide and 261 mg (0.56 mmol) of staurosporin in 10 ml of N,N'-dimethylformamide give, after a reaction time of a total of 46 hours (4 hours at 0°, 42 hours at room temperature), purification by column chromatography (30 g of silica gel Si 60, Merck 9385, 0.040–0.063 mm) in methylene chloride/methanol (99:1; 10 ml fractions) and suspending the fractions 145–200 in diethyl ether, N-(1-α,4,6-O-triacetyl-2-N-acetylmuramyl)staurosporin in the form of beige crystals of m.p. 199°–204° (sintering from 182°) having a residual water content of 1.22 mol and containing a small amount of diethyl ether; $[\alpha]_D^{20} = +144.7° \pm 2.2°$ (c=0.456; methanol). The starting material is obtained as follows:

Step 29.1: Analogously to Example 28, Step 28.1, 570 mg (1.47 mmol) of 4,6-O-diacetyl-2-N-acetylmuramic acid (1-α-anomer) having a residual water content of 0.55 mol and 308 mg (3.02 mmol; 0.286 ml) of acetic anhydride in 20 ml of absolute pyridine give, after a reaction time of 42 hours at room temperature, purification of the crude product by column chromatography on 100 g of silica gel Si 60 (Merck 9385, 0.040-0.063 mm) in chloroform/methanol/water (70:30:5; 10 ml fractions) and crystallisation of the fractions 43-105 from 21 ml of methylene chloride/diethyl ether (1:20), 1-α,4,6-O-triacetyl-2-N-acetylmuramic acid in the form of colourless crystals of m.p. 87.4°-90.5° (sintering from 84°) having a residual water content of 0.14 mol; $[\alpha]_D^{20} = +102.4° \pm 2.0°$ (c=0.494; methanol).

EXAMPLE 30

In a manner analogous to the methods described in the present application the following compounds are obtained:

a) N-(1-Deoxy-6-O-acetyl-2-N-acetylmuramyl)-staurosporin having a residual water content of 1.73 mol, m.p. 225°-227° (sintering from 218°; from ethyl acetate:n-pentane=1:5), $[\alpha]_D^{20} = +197.4° \pm 1.8°$ (c=0.549; methanol), b) N-(1-Deoxy-6-O-mesyl-2-N-acetylmuramyl)-staurosporin having a residual water content of 1.78 mol, m.p. 231°-233° (sintering from 222°; from ethyl acetate), $[\alpha]_D^{20} = +188.8° \pm 2.1°$ (c=0.472; methanol), c) N-(1-Deoxy-6-O-toluolsulfonyl-2-N-acetylmuramyl)staurosporin having a residual water content of 0.83 mol, m.p. 219°-221° (from ethyl acetate), $[\alpha]_D^{20} = +192.1° \pm 2.0°$ (c= 0.507; chloroform:methanol=1:1), d) N-(1-Deoxy-6-azido-2-N-acetylmuramyl)staurosporin having a residual water content of 0.82 mol, m.p. 291°-293° (from ethyl acetate), $[\alpha]_D^{20} = +216.9° \pm 2.1°$ (c=0.474; chloroform:methanol=1:1), and e) N-(1-Deoxy-6-O-mesyl-2-N-acetylmuramyl)-staurosporin methanesulfonate having a residual water content of 3.90 mol, m.p. 255°-257° (sintering from 252°; from methanol:ethyl acetate=3:25), $[\alpha]_D^{20} = +175.0° \pm 1.9°$ (c=0.540; methanol).

EXAMPLE 31

Tablets comprising 20 mg of active ingredient, for example one of the compounds of the formula I described in the preceding examples, are prepared in the customary manner in the following composition:

Composition:

| | |
|---|---|
| Active ingredient | 20 mg |
| Wheat starch | 60 mg |
| Lactose | 50 mg |
| Colloidal silica | 5 mg |
| Talc | 9 mg |
| Magnesium stearate | 1 mg |
| | 145 mg |

Preparation: The active ingredient is mixed with some of the wheat starch, the lactose and colloidal silica, and the mixture is passed through a sieve. Some more wheat starch is made into a paste with 5 times the amount of water in a water bath, and the powder mixture is kneaded with this paste until a slightly kneadable composition has been formed.

The kneadable composition is pressed through a sieve of mesh size approx. 3 mm and dried, and the dry granules obtained are passed again through a sieve. The remainder of the wheat starch, the talc and the magnesium stearate are thereinafter admixed, and the mixture is compressed to give notched tablets of 145 mg weight.

What is claimed is:

1. A staurosporin derivative of the formula I

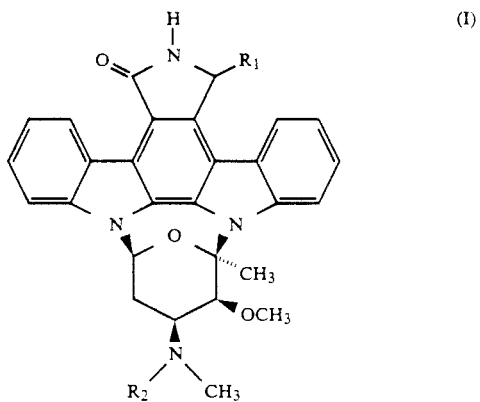

in which $R_1$ is hydrogen, hydroxyl, lower alkoxy or oxo and $R_2$ is a radical of the formula II

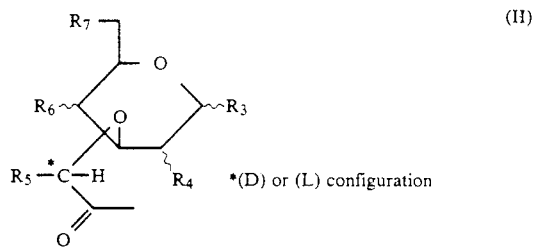

*(D) or (L) configuration in which the configuration of the sugar moiety is derived from D-glucose, D-galactose or D-mannose, and $R_3$ is hydrogen, hydroxyl, lower alkanoyloxy, lower alkoxy, or benzyloxy, benzoyloxy or phenyloxy, each of which is unsubstituted or substituted in the phenyl moiety by halogen, hydroxyl, trifluoromethyl, lower alkyl or lower alkoxy, $R_4$ is hydroxyl, lower alkanoyloxy, benzoyloxy, benzyloxy, amino, lower alkylamino, di-lower alkylamino, lower alkoxycarbonylamino, $C_2$-$C_{20}$alkanoylamino, or benzoylamino, benzyloxycarbonylamino or phenyloxycarbonylamino, each of which is unsubstituted or substituted in the phenyl moiety by halogen, hydroxyl, trifluoromethyl, lower alkyl or lower alkoxy, $R_5$ is hydrogen or lower alkyl, $R_6$ is hydroxyl which is free or esterified with an aliphatic $C_2$-$C_{22}$ carboxylic acid, or is lower alkoxycarbonyloxy, lower alkylsulfonyloxy, amino which is free or acylated with an aliphatic $C_2$-$C_{22}$carboxylic acid, or is lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an aliphatic $C_2$-$C_{22}$carboxylic acid, or is lower alkoxycarbonyloxy, lower alkylsulfonyloxy, azido, amino which is free or acylated with an aliphatic $C_2$-$C_{22}$carboxylic acid, or is lower alkylamino, di-lower alkylamino, lower alkoxycarbonylamino, carbamoylamino, or is benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, or an acid addition salt of such a compound with at least one salt-forming group.

2. A compound of the formula I according to claim 1 in which $R_3$ is hydroxyl, lower alkanoyloxy, lower alkoxy, or benzyloxy, benzoyloxy or phenyloxy, each of which is unsubstituted or substituted in the phenyl moiety by halogen, hydroxyl, trifluoromethyl, lower alkyl or lower alkoxy, and $R_4$ is amino, lower alkylamino, di-lower alkylamino, lower alkoxycarbonylamino, $C_2$-$C_{20}$alkanoylamino, or benzoylamino, benzyloxycarbonylamino or phenyloxycarbonylamino, each of which is unsubstituted or substituted in the phenyl moiety by halogen, hydroxyl, trifluoromethyl, lower alkyl or lower alkoxy, or an acid addition salt of such a compound with at least one salt-forming group.

3. A compound of the formula I according to claim 1, in which $R_6$ is hydroxyl which is free or esterified with an unsubstituted aliphatic $C_2$-$C_{22}$carboxylic acid, or is lower alkoxycarbonyloxy, lower alkylsulfonyloxy, amino which is free or acylated with an unsubstituted aliphatic $C_2$-$C_{22}$carboxylic acid, or is lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an unsubstituted aliphatic $C_2$-$C_{22}$carboxylic acid, lower alkoxycarbonyloxy, lower alkylsulfonyloxy, azido, amino which is free or acylated with an unsubstituted aliphatic $C_2$-$C_{22}$carboxylic acid, or is lower alkylamino, di-lower alkylamino, lower alkoxycarbonylamino, carbamoylamino, or benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, or an acid addition salt of such a compound with at least one salt-forming group.

4. A compound of the formula I according to claim 2, in which $R_6$ is hydroxyl which is free or esterified with an unsubstituted aliphatic $C_2$-$C_{22}$carboxylic acid, or is lower alkoxycarbonyloxy, lower alkylsulfonyloxy, amino which is free or acylated with an unsubstituted aliphatic $C_2$-$C_{22}$carboxylic acid, or is lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an unsubstituted aliphatic $C_2$-$C_{22}$carboxylic acid, lower alkoxycarbonyloxy, lower alkylsulfonyloxy, azido, amino which is free or acylated with an unsubstituted aliphatic $C_2$-$C_{22}$carboxylic acid, or is lower alkylamino, di-lower alkylamino, lower alkoxycarbonylamino, carbamoylamino, or benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, or an acid addition salt of such a compound with at least one salt-forming group.

5. A compound of the formula I according to claim 1, in which $R_1$ is hydrogen and $R_6$ is hydroxyl which is free or esterified with an unbranched $C_2$-$C_{22}$alkanoic acid or an unbranched $C_2$-$C_{22}$alkenoic acid, or is lower alkoxycarbonyloxy, lower alkylsulfonyloxy, amino which is free or acylated with an unbranched $C_2$-$C_{22}$alkanoic acid or an unbranched $C_2$-$C_{22}$alkenoic acid, lower alkoxycarbonylamino, azido, or benzoyloxy, benzyloxycarbonyloxy, benzoylamino, benzyloxycarbonylamino or phenylsulfonyloxy, each of which is unsubstituted or substituted in the phenyl moiety by halogen, hydroxyl, trifluoromethyl, lower alkyl or lower alkoxy, and $R_7$ is hydroxyl which is free or esterified with an unbranched $C_2$-$C_{22}$alkanoic acid or an unbranched $C_2$-$C_{22}$alkenoic acid, or is lower alkoxycarbonyloxy, lower alkylsulfonyloxy, azido, amino which is free or acylated with an unbranched $C_2$-$C_{22}$alkanoic acid or an unbranched $C_2$-$C_{22}$alkenoic acid, or is lower alkylamino, di-lower alkylamino, lower alkoxycarbonylamino, carbamoylamino, or benzoyloxy, benzyloxycarbonyloxy, phenylsulfonyloxy, benzoylamino, benzylamino or benzyloxycarbonylamino, each of which is unsubstituted or substituted in the phenyl moiety by halogen, hydroxyl, trifluoromethyl, lower alkyl, lower alkoxy or lower alkoxycarbonyl, or an acid addition salt of such a compound with at least one salt-forming group.

6. A compound of the formula I according to claim 1, in which the configuration of the sugar moiety is derived from D-glucose, or an acid addition salt of such a compound with at least one salt-forming group.

7. A compound of the formula I according to claim 2, in which the configuration of the sugar moiety is derived from D-glucose, or an acid addition salt of such a compound with at least one salt-forming group.

8. A compound of the formula I according to claim 3, in which the configuration of the sugar moiety is derived from D-glucose, or an acid addition salt of such a compound with at least one salt-forming group.

9. A compound of the formula I according to claim 4, in which the configuration of the sugar moiety is derived from D-glucose, or an acid addition salt of such a compound with at least one salt-forming group.

10. A compound of the formula I according to claim 1 which has the (D) configuration on the C* atom, or an acid addition salt of such a compound with at least one salt-forming group.

11. A compound of the formula I according to claim 1, in which the configuration of the sugar moiety is derived from D-glucose, $R_1$ is hydrogen and $R_2$ is a radical of the formula II in which $R_3$ is hydrogen, hydroxyl, benzyloxy, lower alkoxy or lower alkanoyloxy, $R_4$ is lower alkanoylamino, $R_5$ is lower alkyl or hydrogen, $R_6$ is hydroxyl or lower alkanoyloxy and $R_7$ is hydroxyl, lower alkysulfonyloxy, azido, amino or alkanoyloxy having up to 24 C atoms, or an acid addition salt of such a compound with at least one salt-forming group.

12. A compound of the formula I according to claim 1, in which the configuration of the sugar moiety is derived from D-glucose, $R_1$ is hydrogen and $R_2$ is a radical of the formula II in which $R_3$ is hydrogen, hydroxyl, benzyloxy, lower alkoxy or lower alkanoyloxy, $R_4$ is $C_1$-$C_4$alkanoylamino, $R_5$ is $C_1$-$C_4$alkyl or hydrogen, $R_6$ is hydroxy or lower alkanoyloxy and $R_7$ is hydroxyl, methylsulfonyloxy, azido, amino or alkanoyloxy having up to 24 C atoms, or an acid addition salt of such a compound with at least one salt-forming group.

13. A compound of the formula I according to claim 1, in which the configuration of the sugar moiety is derived from D-glucose, $R_1$ is hydrogen and $R_2$ is a radical of the formula II in which $R_3$ is hydroxyl, benzyloxy or lower alkoxy, $R_4$ is lower alkanoylamino, $R_5$ is lower alkyl or hydrogen, $R_6$ is hydroxyl and $R_7$ is hydroxyl, lower alkylsulfonyloxy, azido or amino, or an acid addition salt of such a compound with at least one salt-forming group.

14. A compound of the formula I according to claim 1 or a pharmaceutically acceptable acid addition salt of such a compound with at least one salt-forming group selected from N-(1-α-O-Benzyl-2-N-acetylmuramyl)staurosporin,
N-(2-N-Acetyl-muramyl)staurosporin,
N-(6-0-Mesyl-1-α-O-benzyl-2-N-acetylmuramyl)-staurosporin,
N-(6-Azido-1-α-O-benzyl-2-N-acetyl-6-deoxymuramyl)staurosporin,
N-(6-Amino-1-α-O-benzyl-2-N-acetyl-6-deoxymuramyl)staurosporin or a pharmaceutically acceptable acid addition salt thereof,
N-(6-Amino-6-deoxy-2-N-acetylmuramyl)staurosporin or a pharmaceutically acceptable acid addition salt thereof,
N-(6-O-Mesyl-2-N-acetylmuramyl)staurosporin,
N-(2-N-Acetyl-demethylmuramyl)staurosporin,
N-(1-α-O-Benzyl-2-N-acetylhomomuramyl)staurosporin,
N-(1-α-O-Benzyl-2-N-acetyl-L-homomuramyl)staurosporin,
the 1-α-anomer of N-(2-N-acetyl-L-homomuramyl)-staurosporin,
N-(1-α-O-Benzyl-4,6-O-diacetyl-2-N-acetylmuramyl)-staurosporin,
N-(1-α-O-Benzyl-4-O-acetyl-6-O-stearoyl-2-N-acetylmuramyl)staurosporin,
N-(1-Deoxy-2-N-acetylmuramyl)staurosporin,
the 1-α-anomer of N-(4-O-acetyl-6-O-stearoyl-2-N-acetylmuramyl)staurosporin,
the 1-α-anomer of N-(4,6-O-diacetyl-2-N-acetylmuramyl)staurosporin,
N-(1-α,4-O-diacetyl-6-O-stearoyl-2-N-acetylmuramyl)-staurosporin,
N-(1-α,4,6-O-Triacetyl-2-N-acetylmuramyl)staurosporin,
N-(1-Deoxy-6-O-acetyl-2-N-acetylmuramyl)staurosporin,
N-(1-Deoxy-6-O-mesyl-2-N-acetylmuramyl)staurosporin,
N-(1-Deoxy-6-O-toluolsulfonyl-2-N-acetylmuramyl)-staurosporin,
N-(1-Deoxy-6-azido-2-N-acetylmuramyl)staurosporin, and
N-(1-Deoxy-6-O-mesyl-2-N-acetylmuramyl)staurosporin.

15. A pharmaceutical composition for the treatment of diseases which respond to an inhibition of proteinkinase C in a warm-blooded animal, which comprises a proteinkinase-C-inhibiting effective amount of a compound of the formula I according to claim 1 or a pharmaceutically acceptable acid addition salt of such a compound with at least one salt-forming group together with a pharmaceutically acceptable carrier.

16. A method for inhibiting proteinkinase C in a warm-blooded animal requiring such a treatment, whereby an effective proteinkinase-C-inhibiting dose of a compound of the formula I according to claim 1 or of a pharmaceutically acceptable acid addition salt of such a compound with at least one salt-forming group is administered to this warm-blooded animal.

* * * * *

UNITED STATES PATENT AND TRADEMARK OFFICE
CERTIFICATE OF CORRECTION

PATENT NO. : 5,264,431
DATED : Nov. 23rd, 1993
INVENTOR(S) : Wacker et al

It is certified that error appears in the above-identified patent and that said Letters Patent is hereby corrected as shown below:

Column 38:
In claim 11, line 54, replace "alkysulfonyloxy" with
--alkylsulfonyloxy--

Signed and Sealed this

Seventeenth Day of May, 1994

Attest:

BRUCE LEHMAN

Attesting Officer     Commissioner of Patents and Trademarks